(12) United States Patent
Liu

(10) Patent No.: US 9,907,896 B2
(45) Date of Patent: Mar. 6, 2018

(54) APPARATUS AND PROCESS FOR PREPARATION OF SMALL WATER CLUSTER AND SMALL MOLECULAR CLUSTER WATER PREPARED THEREFROM

(71) Applicant: TAIPEI MEDICAL UNIVERSITY, Taipei (TW)

(72) Inventor: Yu-Chuan Liu, Taipei (TW)

(73) Assignee: TAIPEI MEDICAL UNIVERSITY, Taipei (TW)

(*) Notice: Subject to any disclaimer, the term of this patent is extended or adjusted under 35 U.S.C. 154(b) by 789 days.

(21) Appl. No.: 14/309,486

(22) Filed: Jun. 19, 2014

(65) Prior Publication Data

US 2014/0377808 A1   Dec. 25, 2014

(30) Foreign Application Priority Data

Jun. 21, 2013 (TW) .............................. 102122241 A

(51) Int. Cl.
| | | |
|---|---|---|
| *A61M 1/16* | (2006.01) |
| *C12P 19/34* | (2006.01) |
| *C01B 5/00* | (2006.01) |
| *B01J 19/08* | (2006.01) |
| *C02F 1/30* | (2006.01) |

(Continued)

(52) U.S. Cl.
CPC .......... *A61M 1/1656* (2013.01); *B01J 19/088* (2013.01); *C01B 5/00* (2013.01); *C02F 1/30* (2013.01); *C12P 19/34* (2013.01); *A61M 2202/0413* (2013.01); *A61M 2205/75* (2013.01); *B01J 2219/0894* (2013.01); *C02F 1/005* (2013.01); *C02F 1/48* (2013.01); *C02F 2103/026* (2013.01); *C02F 2305/08* (2013.01); *C02F 2305/10* (2013.01)

(58) Field of Classification Search
CPC .................. A61M 1/1656; A61M 1/16; A61M 2202/0413; A61M 2205/75; C12P 19/34; C01B 5/00; B01J 19/088; B01J 2219/0894; C02F 1/30; C02F 2305/10; C02F 1/005; C02F 1/48
See application file for complete search history.

(56) References Cited

U.S. PATENT DOCUMENTS

| | | | |
|---|---|---|---|
| 5,800,576 A | 9/1998 | Johnson et al. |
| 2005/0061743 A1 | 3/2005 | Buttner |
| (Continued) | | |

FOREIGN PATENT DOCUMENTS

| | | |
|---|---|---|
| CN | 2389879 Y | 8/2000 |
| CN | 1621388 A | 6/2005 |
| (Continued) | | |

OTHER PUBLICATIONS

Office action and search report dated Jan. 27, 2016 for counterpart Taiwan application 103121454.

(Continued)

*Primary Examiner* — Walter D. Griffin
*Assistant Examiner* — Cameron J Allen
(74) *Attorney, Agent, or Firm* — WPAT, P.C., Intellectual Property Attorneys; Anthony King

(57) ABSTRACT

The invention provides an apparatus of treating water to obtain small water cluster, which comprises one or more illumination devices and one or more holders holding metal particles. The invention also provides a method of preparing the small water cluster and the small water cluster prepared from the apparatus or the method.

4 Claims, 18 Drawing Sheets

(51) Int. Cl.
  *C02F 1/00* (2006.01)
  *C02F 1/48* (2006.01)
  *C02F 103/02* (2006.01)

(56) References Cited

U.S. PATENT DOCUMENTS

| | | |
|---|---|---|
| 2011/0039951 A1 | 2/2011 | Price-Gallagher et al. |
| 2011/0089049 A1 | 4/2011 | Musson |
| 2011/0218251 A1 | 9/2011 | Lo et al. |
| 2013/0056355 A1 | 3/2013 | Hou |

FOREIGN PATENT DOCUMENTS

| | | |
|---|---|---|
| CN | 202030602 U | 11/2011 |
| TW | M382845 | 6/2010 |
| WO | WO 91/06894 A1 | 5/1991 |

OTHER PUBLICATIONS

English translation of the search report dated Jan. 27, 2016 for counterpart Taiwan application 103121454.
Office action dated Sep. 21, 2016 for counterpart China application 201410280968.4.
English abstract translation of the office action dated Sep. 21, 2016 for counterpart China application 201410280968.4.
English abstract translation of CN202030602U.
Zhou, Xuemei et al., Surface plasmon resonance-mediated photocatalysis by noble metal-based composites under visible light, Journal of Materials Chemistry, 2012, vol. 22, 21337-21354.
Office action dated Apr. 6, 2017 for counterpart China application 201410280968.4.
English abstract translation of the office action dated Apr. 6, 2017 for counterpart China application 201410280968.4.
English abstract translation of CN1621388A.
English abstract translation of CN2389879Y.

APPARATUS AND PROCESS FOR PREPARATION OF SMALL WATER CLUSTER AND SMALL MOLECULAR CLUSTER WATER PREPARED THEREFROM

FIELD OF THE INVENTION

The invention relates to an apparatus and process for treating water and the water treated by the apparatus or process. Particularly, the invention provides an apparatus and process for preparing small water cluster and the small water cluster treated by the apparatus or process.

BACKGROUND OF THE INVENTION

Water ($H_2O$) is an inorganic material consisting of two elements, hydrogen and oxygen. Water is important for all organisms and is an essential element of organisms. The elements and molecular structure bestow it with unique properties, particularly the formation of hydrogen bond. In the structure of water, there are two receptors and two donors of forming hydrogen bonds, respectively; and various structures between water molecules are formed by hydrogen bond, such as tetrahedron structure like ice, dimer and polymer. Therefore, at the microenvironment level, the water molecule is called a "water cluster," which is a water molecule cluster formed with discontinuous hydrogen structure. The hydrogen bonds of small water cluster are cleaved more easily to form individual water molecules, so the small water cluster has stronger diffusion power and faster absorption rate. Therefore, compared to the large water cluster, the small water cluster can readily pass through the water channel on a cell membrane and allow an ingredient to enter a cell easily and improve metabolism.

After water is boiled or gasified, it will become small molecule water; however, after cooling it to room temperature, water molecules will form a large molecule cluster. A water cluster has an antioxidant effect after hydrogen gas is added; however, due to low solubility of hydrogen gas, the hydrogen gas will rapidly effuse to atmosphere. The solubility of solids and gas in water can be increased by elevating temperature and pressure; however, an additional apparatus and process are necessary to achieve this effect. More, after it returns to normal temperature and pressure, the solubility will return to the original state without increased solubility.

Taiwan Patent No. M382845 discloses a filtration element with a composite layer and a filtration apparatus having the element, said composite layer consisting of nano noble metal chitosan composite, and the composite comprising a chitosan substrate and a number of nano noble metal particles adsorbed on the surface of the chitosan substrate. The harmful substances in a fluid can be removed after passing through the composite having the substrate and nano noble metal so as to achieve antibacteria and deodorization effects. Furthermore, the filtration and adsorption are improved in view of the adsorption of impurities by chitosan. However, the water treated by the apparatus still cannot achieve satisfactory small water cluster.

U.S. Pat. No. 5,800,576 provides water cluster compositions characterized by high oxygen reactivity due to protruding, delocalized pπ orbitals. The patent application uses a hypersonic nozzle containing nickel or nickel alloy, which is different from that of the prior art, to destroy the interaction between water molecules when water passes through the nozzle to obtain water clusters containing 5 to 300 water molecules and having high oxygen reactivity. However, the property only exists in the water microdroplets formed by instant spray.

US 20110218251 A1 discloses a product having solid stable water clusters including a plurality of water molecules connected with one another by electrical dipole interaction via internal electric field of ions and having a permanent electric dipole moment with an electrical field surrounding the solid stable water clusters. The patent application discloses a product with stable solid water clusters, each sized from a nanometer to a micrometer and formed by the electrical dipole interaction surrounding the water cluster. The chamber having ultrapure water is filled with argon gas to avoid contact with carbon dioxide. After an additive (such as sodium chloride, vitamin, amino acid, hormone, protein, enzyme, polypeptide, polysaccharide, DNA, RNA) is introduced to the chamber, electrical dipole interaction occurs between the additive and water to form stable water clusters. However, the need in the patent application, for an additive means the resulting water is not pure water.

US 20110089049 A1 provides an electrolytic method for treatment of water to increase the dissolved oxygen content; the method further aids the distribution and exposure of radicals through the water cluster. The patent application discloses a method of obtaining a single water cluster by confining a water molecule in an environment of nano-materials including nano-carbon tube or grapheme nanolayer and containing nitrogen, alloy, palladium, palladium-gold or palladium-silver, and the size of the water cluster is 0.5 to 100 nanometers. However, the method of the patent application cannot provide water continuously.

US 20110039951A1 discloses a method including providing a nano-environment and confining heavy or light water in the nano-environment such that at least one water cluster forms. However, the water treated by the above method cannot achieve satisfactory small water cluster.

US 20130056355A1 provides a water treatment system based on electric and magnetic fields, which employs water to pass through a pipe containing a rare earth alloy formed by lanthanum, yttrium, cerium, praseodymium, neodymium, samarium, titanium and zinc metal alloy and excites electrons of water to form an electric field and then pass through a pipe with a permanent magnet to create electric and magnetic fields to break hydrogen bonds between partial water molecules. However, the water treated by the above system cannot achieve satisfactory small water cluster. Moreover, too many various rare earth species are required.

Therefore, there remains a need to develop a smaller water cluster in the art to obtain a small water cluster having increased diffusion power and better absorption rate, which is more beneficial to health.

SUMMARY OF THE INVENTION

The invention provides a water treatment apparatus for preparing small water cluster, comprising one or more illumination devices and one or more holders holding metal particles capable of surface plasma resonance. Preferably, the holder is a hollow light transparent column with one or more inlets and one or more outlets and the light transparent column is filled with metal particles capable of surface plasmon resonance. Accordingly, the invention provides a method for preparing small water cluster by using the apparatus of the invention.

The invention also provides a small water cluster produced from the apparatus or method of the invention. In one embodiment, the small water cluster has a specific Raman spectrum, infrared absorption spectrum, evaporation rate, solubility, maximum amount of dissolved oxygen and vapor pressure.

DETAILED DESCRIPTION OF THE INVENTION

Figure 1:
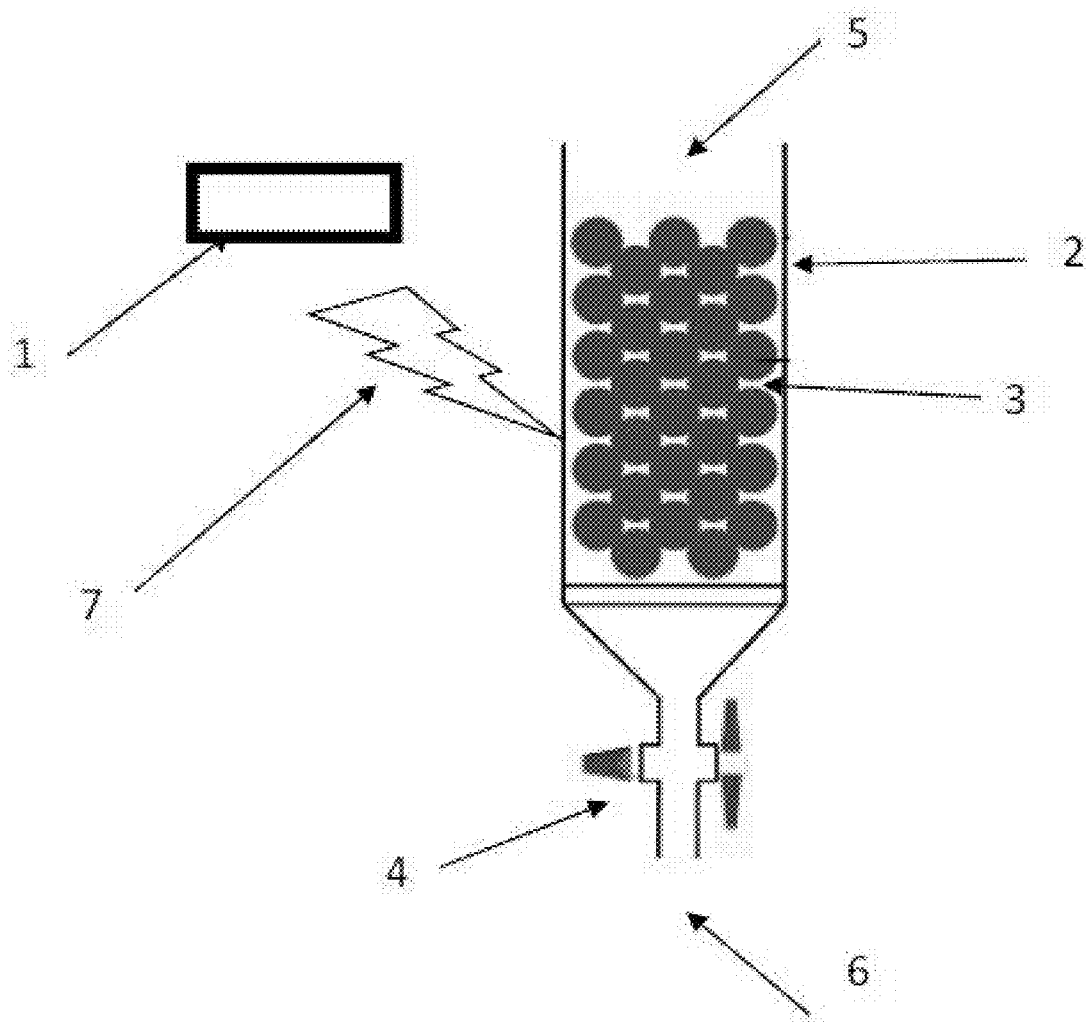
FIG. 1 refers to an illustrative drawing of one embodiment of the apparatus of the invention.

Due to the formation of hydrogen bonds, water exists in the form of tetrahedrally hydrogen-bonded water molecules (water cluster). The hydrogen bond in water will weaken as the water molecule receives energy, is subjected to high pressure or comprises an electrolyte so that the tetrahedral structure of the water is destroyed and small water clusters are formed. The invention combines the plasmon resonance effect of nano-metal particles and illumination providing energy to increase plasmon resonance effect to provide hot electrons to break hydrogen bonds in a water molecule cluster to form small water cluster with smaller molecular clusters.

In one aspect, the invention provides a water treatment apparatus for preparing small water cluster, comprising one or more illumination devices and one or more holders holding metal particles capable of surface plasma resonance, provided that the holder allows illumination of the metal particles.

According to the invention, any holder suitable to hold the metal particles of the invention can be used in the apparatus of the invention. Preferably, the holder is a container, transparent column or solid support. In one embodiment, the transparent column of the apparatus has one or more inlets and one or more outlets; preferably, the outlet of the column is narrower than the inlet of the column and has a switching control valve. In another embodiment, the solid support is a polymer support. In another embodiment, the container is a hollow container or a hollow container having one or more inlets and one or more outlets. Preferably, the hollow container is a shallow tray. Preferably, the wall of the hollow container is transparent. In one embodiment, the illumination device is a light source providing a wavelength ranging from 100 nm to 3,000 nm. Preferably, the light source provides a wavelength ranging from 380 nm to 780 nm; more preferably, 500 nm to 600 nm (preferably, 380 nm to 480 nm for nano-silver). According to one embodiment of the invention, the illumination device is a daylight lamp, LED lamp, lamp bulb, mercury lamp, metal halide lamp, sodium lamp or halogen lamp; preferably, LED green lamp.

According to the invention, any transparent material can be used to prepare the transparent column of the invention. According to one embodiment of the invention, the transparent column is a glass column or plastic column.

According to the invention, the holder holds or fills with metal particles capable of surface plasma resonance. Plasma is a physical state that occurs between metal and dielectric surfaces, and is formed by exciting a surface plasmon wave (SPW) between a thin metal layer and dielectric surface by employing electrons or photons. A TM-wave of incident light excites free electrons between the metal and surface of the medium by a coupler so that collective longitudinal resonance can be formed. According to one embodiment of the invention, the metal particle is a nano-metal particle; preferably, nano-gold particle, nano-silver particle, nano-platinum particle, nano-rhodium particle, nano-copper particle, nano-nickel particle, nano-zirconium particle, nano-alloy particle (such as ZrNiCu alloy), nano-$TiO_2$ particle or a combination thereof. More preferably, it is a nano-gold particle, nano-silver particle, nano-gold/silver particle or nano-gold/$TiO_2$ particle. According to another embodiment of the invention, the nano-metal particle can be combined with another material to form a composite; the metal in the composite is preferably gold, silver, platinum, rhodium, copper, nickel, zirconium or an alloy and the other material in the composite is preferably chitosan or ceramic. The composite includes, but is not limited to, nano-gold/ceramic particles or nano-gold/chitosan particles. According to another embodiment, the nano-metal particle is in a size of 0.1 nm to 1,000 nm; preferably, 1 nm to 100 nm. In another embodiment, the particle of the invention is spherical, cylindrical, elliptical, cuboidal or cubical shape.

Any known method can be used in the preparation of the nano-particle of the invention. For example, laser ablation method, metal vapor synthesis method and chemical reduction method (such as electrochemical reduction and sono-electrochemical reduction method).

In another aspect, the invention provides a method for preparing a small water cluster, comprising providing a holder holding a plurality of metal particles capable of surface plasma resonance, contacting water with the nano-metal particles and illuminating the nano-metal particles to obtain the small water cluster. Preferably, the method is performed by using the apparatus of the invention; particularly, using any of embodiments of the apparatus of the invention described herein. The method of using the apparatus of the invention introduces water to the holder of the apparatus of the invention and illuminates the holder with the illumination device of the invention. After water passes through the metal particles, since the metal particles cause surface plasmon resonance (SPR), after illumination, a specific wavelength (about 538 nm in the invention) of energy can be absorbed to generate SPR effect to break partial hydrogen bonds in a water molecule cluster. The illumination in combination with plasmon resonance weakens the hydrogen bonds of water to form small water cluster. The small water cluster of the invention can stably exist for long time (at least three days) and has special properties and functions.

FIG. 1 is an illustrative figure of the apparatus of the invention. Referring to FIG. 1, the apparatus of the invention has an illumination device 1 and a transparent column 2. The transparent column 2 has an inlet 5 and an outlet 6; the outlet 6 is narrower than the inlet 5. A switching control value 4 is equipped close to the outlet 6. The transparent column 2 fills with nano-gold/ceramic particles 3.

The water to be treated enters into the transparent column 2 from the inlet 5. The illumination device 1 provides energy 7 (provided by daylight lamp or green LED illumination). After the nano-gold/ceramic particles absorb energy at a specific wavelength (for example about 538 nm), the surface plasmon resonance effect occurs to break partial hydrogen bonds of water molecules to form small water cluster. The switching control value 4 of the transparent column 2 is opened to collect the treated small water cluster from the outlet 6.

Figure 2:
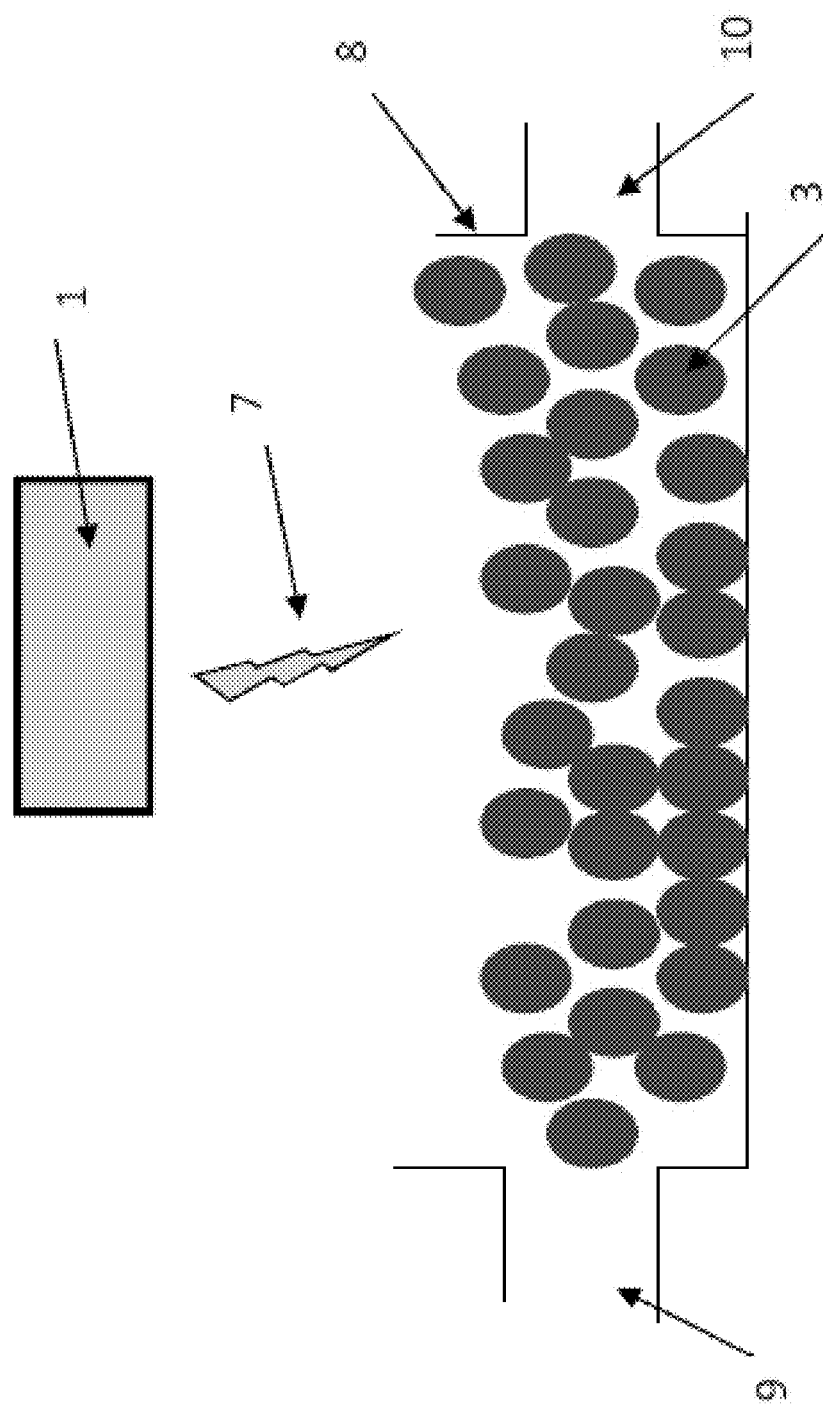
FIG. 2 refers to refers to an illustrative drawing of another embodiment of the apparatus of the invention.

FIG. 2 is an illustrative figure of another embodiment of the apparatus of the invention. Referring to FIG. 2, the apparatus of the invention has an illumination device 1 and an open hollow container 8. The open hollow container 8 has an inlet 9 and an outlet 10. The hollow container 8 fills with nano-gold/ceramic composite particles 3. The water to be treated enters into the hollow container 8 from the inlet 9. The illumination device 1 provides energy 7 by illumination (provided by daylight lamp or green LED illumination). After the nano-gold/ceramic particles absorb energy at a specific wavelength (for example about 538 nm), the surface plasmon resonance effect occurs to break partial hydrogen bonds of water molecules to form small water cluster. Then, the small water cluster is collected from the outlet 10. In another embodiment, the invention provides an apparatus, the devices of which and the connection thereof are similar to FIG. 2, with the difference merely lying in that the hollow container does not have the inlets and outlets.

In one embodiment, the illumination time in the invention is 5 minutes to 480 minutes; preferably, 5 minutes to 240 minutes or 10 minutes to 240 minutes.

In another aspect, the invention provides a small water cluster produced from the apparatus or method of the invention. In one embodiment, the small water cluster has specific Raman spectrum, infrared absorption spectrum, evaporation rate and solubility etc.

Raman spectroscopy is used to study interaction of water molecules. Raman shift of about 2600 to 4000 $cm^{-1}$ represents the OH vibration of water molecules, and five bands can be identified within the range by Gaussian function deconvolution. The deconvolution of different water samples is to fix the positions of the five bands, and the central points of the five bands are about 3018 $cm^{-1}$, about 3223 $cm^{-1}$, about 3393 $cm^{-1}$, about 3506 $cm^{-1}$, and 3624 $cm^{-1}$ in view of the fact that the full width at half maximum (FWHM) is the same of each water sample. The former three positions represent strong hydrogen bond and the latter two positions represent weak hydrogen bond and non-hydrogen bond, respectively (J. Raman Spectrosc. 2009, 40, 1200; Vib. Spectrosc. 2012, 62, pp. 110-114; J. Chem. Phys. 1998, Vol. 108, No. 7, pp. 2669-2675). The integral area of the latter two bands divided by the sum of the integral area of the five bands is defined as the percentage of the non-hydrogen bond level (NHBL) in the water molecule sample. In detail, in the spectrum deconvolution, th signals of OH vibration are set at the positions about 3018 $cm^{-1}$, about 3223 $cm^{-1}$, about 3393 $cm^{-1}$, about 3506 $cm^{-1}$, and 3624 $cm^{-1}$, and the full width at half maximum (FWHM) is the same of each water sample. The non-hydrogen bond level is obtained by the integral area at the about 3506 $cm^{-1}$ and about 3624 $cm^{-1}$ positions divided by the sum of the integral areas of the five bands at about 3018 $cm^{-1}$, about 3223 $cm^{-1}$, about 3393 $cm^{-1}$, about 3506 $cm^{-1}$, and 3624 $cm^{-1}$ positions.

Generally, the non-hydrogen bond level of deionized water is 21.29%. When hydrogen bonds are broken, the Raman spectrum shows that the band strength (area) of strong hydrogen bond decreases, while the weak the strength (area) of hydrogen bond and non-hydrogen bond increases (J. Chem Phys. 1981, 75, 4264). Therefore, Raman spectrum can be used to show the properties of the small water molecule cluster of the invention. In detail, the central points of the Raman bands in the deconvoluted spectrum on OH vibration of water are at the positions of about 3018 $cm^{-1}$, about 3223 $cm^{-1}$, about 3393 $cm^{-1}$, about 3506 $cm^{-1}$, and 3624 $cm^{-1}$ respectively, and the non-hydrogen bond level obtained by the integral area at the about 3506 $cm^{-1}$ and about 3624 $cm^{-1}$ positions divided by the sum of the integral areas of the five bands at about 3018 $cm^{-1}$, about 3223 $cm^{-1}$, about 3393 $cm^{-1}$, about 3506 $cm^{-1}$, and 3624 $cm^{-1}$ positions is higher than about 22%; preferably, larger than about 23%, about 24%, about 24.11%, about 25%, about 26%, about 27%, about 28%, about 29%, about 30%, 30.31%, about 31%, about 32%, about 33%, about 34%, or about 35%. More preferably, the non-hydrogen bond level of the small water cluster is about 24% to about 50%, about 24% to about 45%, about 24% to about 40% or about 24% to about 32%. In one embodiment, the Raman spectrum further comprises the Raman shifts at the positions of about 3506 $cm^{-1}$ and 3624 $cm^{-1}$ higher than about 15.0% and about 6%, respectively, wherein the percentage is calculated by the integral area of the band at about 3506 $cm^{-1}$ or at about 3624 $cm^{-1}$ divided by the sum of the integral areas of the five bands at about 3018 cm$^{-1}$, about 3223 cm$^{-1}$, about 3393 cm$^{-1}$, about 3506 cm$^{-1}$, and 3624 cm$^{-1}$ positions; preferably, about 16% and about 7% respectively, or about 16.7% and about 7.3% respectively. In this embodiment, the percentage represents the ratio of the integral area for one band at about 3506 cm$^{-1}$ or at about 3624 cm$^{-1}$ to the sum of the integral areas of the five bands at about 3018 cm$^{-1}$, about 3223 cm$^{-1}$, about 3393 cm$^{-1}$, about 3506 cm$^{-1}$, and 3624 cm$^{-1}$ positions.

The infrared spectrum (IR) showing OH vibration of water ranges from about 3090 to 3640 cm$^{-1}$, which can be divided into two parts; the characteristic peak at wavelength of about 3090 to about 3310 cm$^{-1}$ represents triple hydrogen bond (high density hydrogen bond) and the characteristic peak at wavelength of about 3310 to about 3640 cm$^{-1}$ represents non-hydrogen bond, single hydrogen bond and doublet hydrogen bond (J. Phys. Chem. B, 2012, 116, 10609). According to one embodiment of the invention, the small water cluster has a specific IR spectrum, wherein the characteristic peak of the triple hydrogen bond (about 3090 to about 3310 cm$^{-1}$) of water molecule and that of the non-hydrogen bond, single hydrogen bond and doublet hydrogen bond (about 3310 cm$^{-1}$ to about 3640 cm$^{-1}$) of water molecule shift from about 3170 cm$^{-1}$ (the characteristic peak of deionized water) to about 3175 cm$^{-1}$ and from about 3449 cm$^{-1}$ to about 3454 cm$^{-1}$, respectively. In detail, the characteristic peak of the triple hydrogen bond in the IR spectrum (about 3090 to about 3310 cm$^{-1}$) and the non-hydrogen bond, single hydrogen bond and doublet hydrogen bond in the IR spectrum (about 3310 cm$^{-1}$ to about 3640 cm$^{-1}$) of the water molecule shift from about 3170 cm$^{-1}$ to about 3175 cm$^{-1}$ and from about 3449 cm$^{-1}$ to about 3454 cm$^{-1}$, respectively. Preferably, from about 3170 cm$^{-1}$ to more than about 3183 cm$^{-1}$ and from about 3449 cm$^{-1}$ to more than about 3461 cm$^{-1}$, respectively.

According to another embodiment, compared to the deionized water, the small water cluster of the invention has higher evaporation rate. The evaporation rate of the small water cluster of the invention is more than 3%/hour higher than that of the deionized water; preferably, more than 7.2%/hour higher than that of the deionized water. The preferred range is 7 to 12%/one hour higher than that of the deionized water. The electric resistance is 18.2 MΩ cm using MilliQ system.

According to another embodiment, the solubility of NaCl in the small water cluster of the invention at about 22.8° C. under about 1 atmosphere is more than about 37 g dL$^{-1}$; preferably, about 41.3 g dL$^{-1}$. The preferred range is about 38.5$^{-1}$ to about 40.5 g dL$^{-1}$. According to another embodiment, the maximum amount of dissolved oxygen of the small water cluster of the invention at about 22.8° C. under about 1 atmosphere is more than about 21 mg L$^{-1}$; preferably, about 23.8 mg L$^{-1}$. The preferred range is about 21.5 mg L$^{-1}$ to 23.0 mg L$^{-1}$.

The apparatus and method of the invention can effectively break the strong hydrogen bond structure to form a weak hydrogen bond and non-hydrogen bond structure, which is the structure of the small water cluster of the invention. Thus, the small water cluster of the invention has specific properties and functions. In one embodiment, compared to the deionized water as control (in which the non-hydrogen bond level is about 21.29%), the non-hydrogen bond level of the small water cluster of the invention is about 24.11%. In comparison with the small water cluster of the invention and the deionized water, the non-hydrogen bond level increases about 13% ((24.11%−21.29%)/21.29%×100%).

According to another embodiment, the free OH vibration (non-hydrogen bonding) of the small water cluster of the invention can form a hydrogen bond with polyethylene glycol 400 (PEG 400 having molecule weight of 400). Therefore, the measurement value of the solubility of the small water cluster in PEG 400 is smaller than the preparation value by more than about 2%; preferably, more than about 3%, more than about 4%, more than about 5%, more than about 6%, more than about 7%, more than about 8%, more than about 9% or more than about 10%.

According to another embodiment, the saturated vapor pressure of the small water cluster of the invention at 25° C. is higher than that of the deionized water by more than about 3.0%; preferably, more than about 4%, more than about 5%, more than about 6%, more than about 7%, more than about 8%, more than about 9% or more than about 10%.

Since the small water cluster of the invention is treated by the above-mentioned metal particles, according to another embodiment, the small water cluster of the invention will have metal residue that can be measured by inductively coupled plasma-mass spectrometer (ICP-MS). Preferably, the concentration of the residue is more than about 0.05 ppb; more preferably, more than about 0.1 ppb, more than about 0.2 ppb, more than about 0.3 ppb, more than about 0.4 ppb, more than about 0.5 ppb, more than about 0.6 ppb, more than about 0.7 ppb, more than about 0.8 ppb, more than about 0.9 ppb or more than about 1.0 ppb. The metal concentration in the deionized water is about 0.03 ppb.

The small water cluster of the invention has specific properties different from common water; for example, increased solubility of solid and gas at normal temperature and pressure and weaker hydrogen bond between water molecules. In addition, the small water cluster of the invention at normal temperature and pressure can stably exist for a long time. For example, it can stably exist for at least two days; preferably three days. After the small water cluster of the invention mixes with other components, since the other components can combine with the non-hydrogen bond or weak hydrogen bond of the small water cluster, the small water cluster can retain its form and without aggregating and losing the properties and advantages of small water cluster. Therefore, the small water cluster of the invention has utility. The small water cluster of the invention has specific properties, so it can remove free radicals and inhibit NO release from cell inflammation to achieve anti-oxidation and anti-inflammation. In addition, the small water cluster of the invention can also be used as a hemodialysis solution to increase the removal rate of waste in blood and can be used as water for hemodialysis.

Accordingly, the invention provides a use of the small water cluster of the invention as hemodialysis solution. The invention also provides a method for preparing a hemodialysis solution, comprising contacting a hemodialysis water with nano-metal particles and subjecting the resulting solution to illumination to obtain the small water cluster of the invention and using the resulting small water cluster to prepare the hemodialysis solution. The invention also provides a hemodialysis apparatus, comprising a hemodialysis bag or a hemodialysis column coated with nano-metal particles and an illumination device as mentioned herein. The treatment time for the removal of 70% blood urea nitrogen (BUN) and creatinine (Crea) in the hemodialysis using the small water cluster of the invention can be reduced by 47% and 59%, respectively. In addition, the small water cluster of the invention also can reduce NO production in a lipopolysaccharide (LPS)-induced inflammation reaction so that the hemodialysis is safer and more efficient.

In another aspect, the invention provides use of the small water cluster of the invention in a PCR reaction. Compared to deionized water, the reaction rate can increase more than three-fold when the reaction is conducted with the small water cluster of the invention. This shows that the small water cluster of the invention can enhance PCR reaction.

Since water per se has wide applications, the small water cluster of the invention can be used in cosmetic, aesthetic medical, medical pharmaceutical, energy industries and various chemical and physical products, so it has industrial applicability.

EXAMPLES

Example 1

Preparation of the Small Water Cluster of the Invention

Nano-gold was sintered and deposited on the surface of ceramic particles (92% $SiO_2$, 40 mesh) to prepare nano-gold/ceramic particles. A transparent glass column was filled with 1,000 mL of the nano-gold/ceramic particles. The deionized water flowed through the glass column at a flow rate of 1 mL/minute under illumination to produce the small water cluster of the invention.

Example 2

Raman Spectrum of the Small Water Cluster of the Invention

Figure 3:
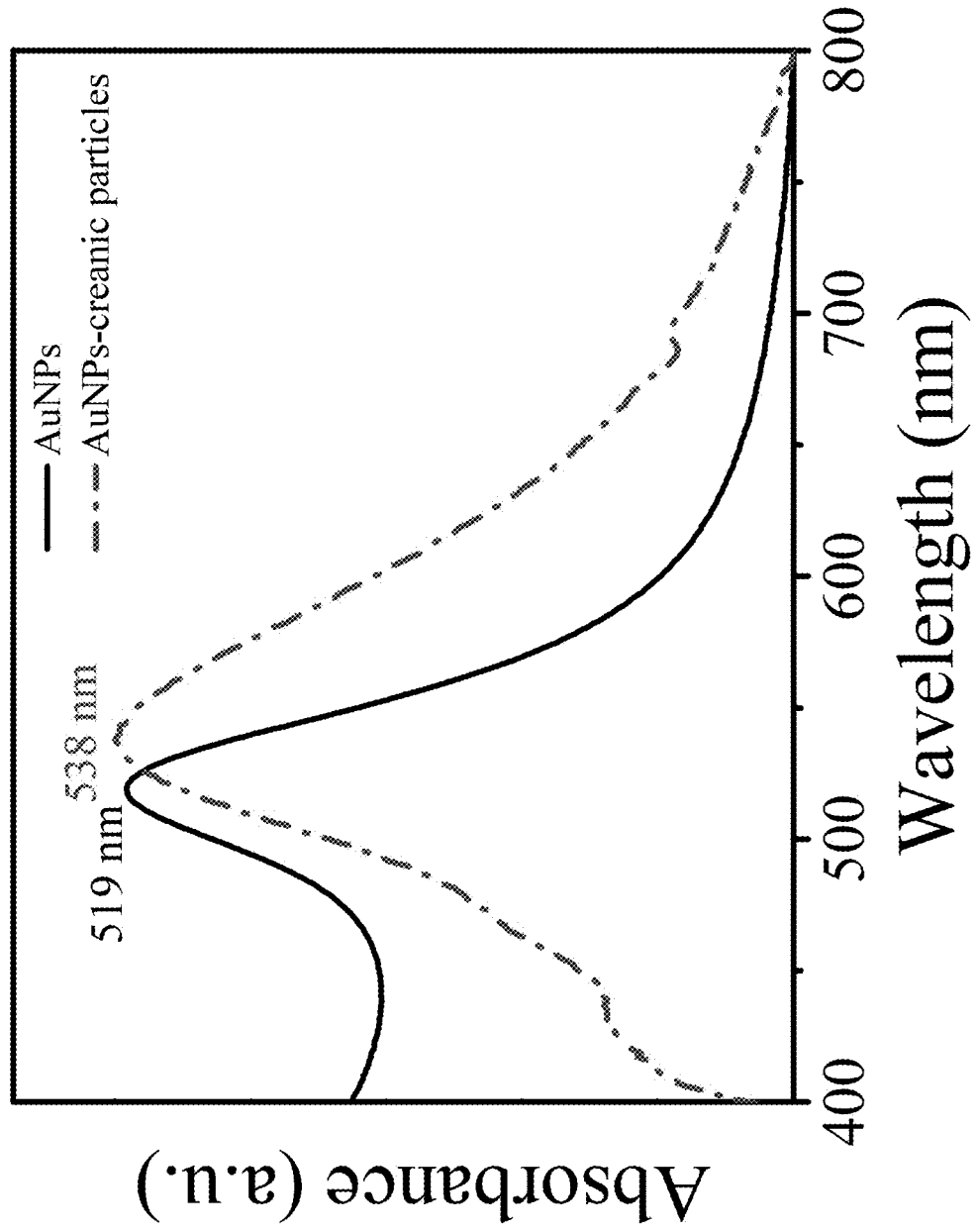
FIG. 3 shows the ultraviolet-visible light absorption spectrum; (a) nano-gold water solution (solid line); (b) ceramic particles deposited with nano-gold (dashed line).

The surface plasmon resonance spectrum of the nano-gold particles was measured by Raman spectroscopy (Perkin Elmer Lambda 800/900). The sample was placed in a 3 mL quartz cell. Water was used as the background value and the scanning rate was 750 nm/minute. The largest absorption band of the nano-gold particle solution was at 519 nm (FIG. 3(a)). The surface plasmon resonance spectrum of the nano-gold/ceramic particles was measured by Raman spectroscopy (Perkin Elmer Lambsa 800/900), the scanning rate was 750 nm/minute and the reflective signals were measured. The moist ceramic particles were used as the background value and the surface plasmon resonance spectrum of the nano-gold/ceramic particle solution was at 538 nm. According to the UV-visible light spectrum, it was found that that the largest absorption band of the red nano-gold solution is at 519 nm and that of the nano-gold deposited on ceramic particles was shifted to 538 nm. As shown in FIG. 3 (b), the energy throughout the entire visible light zones can be absorbed by the nano-gold to produce the SPR effect. However, using the wavelength near 538 nm of the light source produces a stronger SPR effect.

Figure 4:
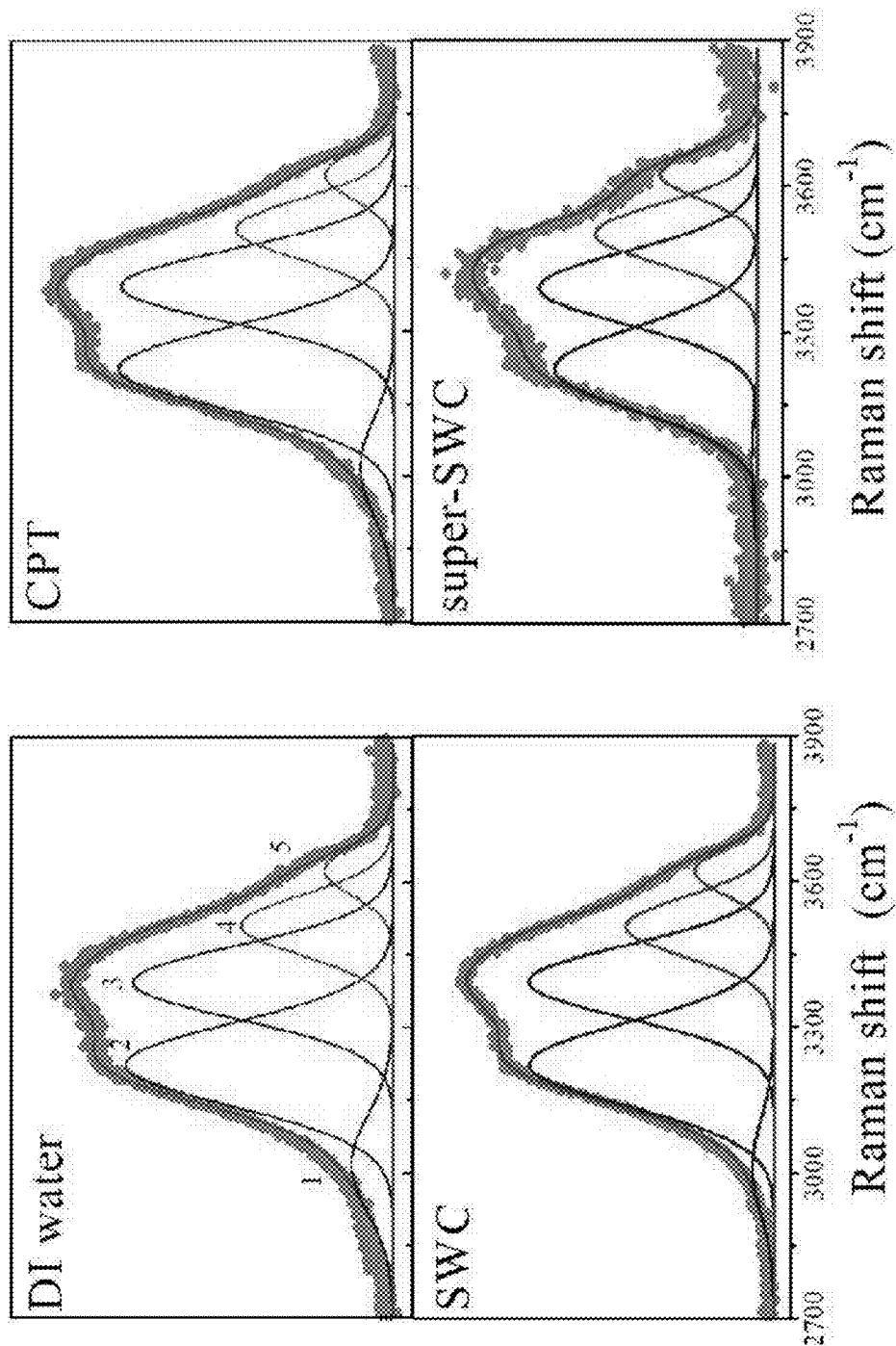
FIG. 4 shows the Raman spectrum of various water samples.

The Raman spectroscopy assay was conducted in de-ionized water (DI water; control), the small water cluster of Example 1 (SWC) and the filtrated water (CPT; positive control), wherein the production of the filtrated water was similar to that of the small water cluster; the difference between them is that the filtrated water flowed through the ceramic particles without nano-gold. The ultra-small water cluster (super-SWC) was prepared by placing the deionized water on the surface of the nano-gold/ceramic particles. 0.5 mL of each of deionized water, the small water cluster and the filtrated water were placed in a round-bottom container with 0.7 cm of circle silver slice, respectively, and a micro Raman spectrometer (UniRAM-Raman) was used for measurement. After the microscope was focused on the surface of the silver slice, the sample was scanned at the wavelength of 532 nm within the range of 2,600 to 4,000 cm-1 at an exposure time of 1 second. After repetitive scanning 30 times, the OH vibration signal can be obtained and spectrum data analysis conducted. The Raman spectrum of the ultra-small water cluster was measured by distributing the deionized water moistened nano-gold-ceramic particles on the silver slice surface, and after focusing the microscope on the surface of the silver slice, scanning the sample under the same conditions as mentioned above. The Raman spectra results are shown in FIG. 4.

Spectrum deconvolution analysis was conducted by setting the OH vibration positions at 3018 $cm^{-1}$, 3223 $cm^{-1}$, 3393 $cm^{-1}$, 3506 $cm^{-1}$ and 3624 $cm^{-1}$ and using the same full width at half maximum (FWHM) for each water sample. The 3506 $cm^{-1}$ and 3624 $cm^{-1}$ positions represent the area of the bands of weak hydrogen bond and non-hydrogen bond. The ratio of this area to that of the entire OH vibration bands is defined as non-hydrogen bond level (including weak-hydrogen bond level and non-hydrogen bond level).

Using deionized water as the control (the non-hydrogen bond level is 21.29%), the non-hydrogen bond level of the small water cluster is 24.11%. The non-hydrogen bond level of the small water cluster represents a 13% increase compared to the deionized water. The non-hydrogen bond level of the filtered water is 21.80%, which is similar to that of the deionized water. The non-hydrogen bond level of the ultra-small water cluster is 30.31%. Compared to the deionized water, the non-hydrogen bond level of the ultra-small water cluster is 42% higher. When the small water cluster is prepared in the absence of illumination, the non-hydrogen bond level is 21.50%, which is similar to the deionized water. Apparently, the illumination is an essential element to prepare the small water cluster. The non-hydrogen bond levels of the small water cluster prepared by using nano-silver, nano-platinum, nano-gold/$TiO_2$ composite and nano-gold/silver composite are 24.36%, 23.76%, 24.17% and 24.94%. This shows that other nano-noble metals and other nano-metal composites can be used to prepare the small water cluster of the invention.

| | Raman shift ($cm^{-1}$) | | | | | Non-hydrogen bond level |
|---|---|---|---|---|---|---|
| | 3018 | 3223 | 3393 | 3506 | 3624 | |
| Deionized water | 5.29% | 40.22% | 33.20% | 15.66% | 5.63% | 21.29% |
| Small water cluster | 3.93% | 38.31% | 33.65% | 16.78% | 7.33% | 24.11% |
| Filtrated water | 5.26% | 40.17% | 33.33% | 15.40% | 5.83% | 21.24% |
| Ultra-small water cluster | 1.19% | 35.30% | 33.20% | 20.36% | 9.95% | 30.31% |
| a | 5.23% | 39.72% | 33.54% | 15.71% | 5.80% | 21.50% |
| b | 4.59% | 37.96% | 33.10% | 17.57% | 6.78% | 24.36% |
| c | 3.72% | 38.49% | 34.04% | 17.59% | 6.17% | 23.76% |
| d | 4.09% | 38.76% | 32.97% | 17.29% | 6.89% | 24.17% |
| e | 4.49% | 35.72% | 34.84% | 20.11% | 4.83% | 24.94% | a: Preparation of small water cluster without illumination
b: Preparation of small water cluster using nano-silver particles
c: Preparation of small water cluster using nano-platinum particles
d: Preparation of small water cluster using nano-gold/nano-$TiO_2$ composite
e: Preparation of small water cluster using nano-gold/nano-silver composite Example 3

Reduction of Hydrogen Bond of Small Water Cluster of the Invention

Figure 5:
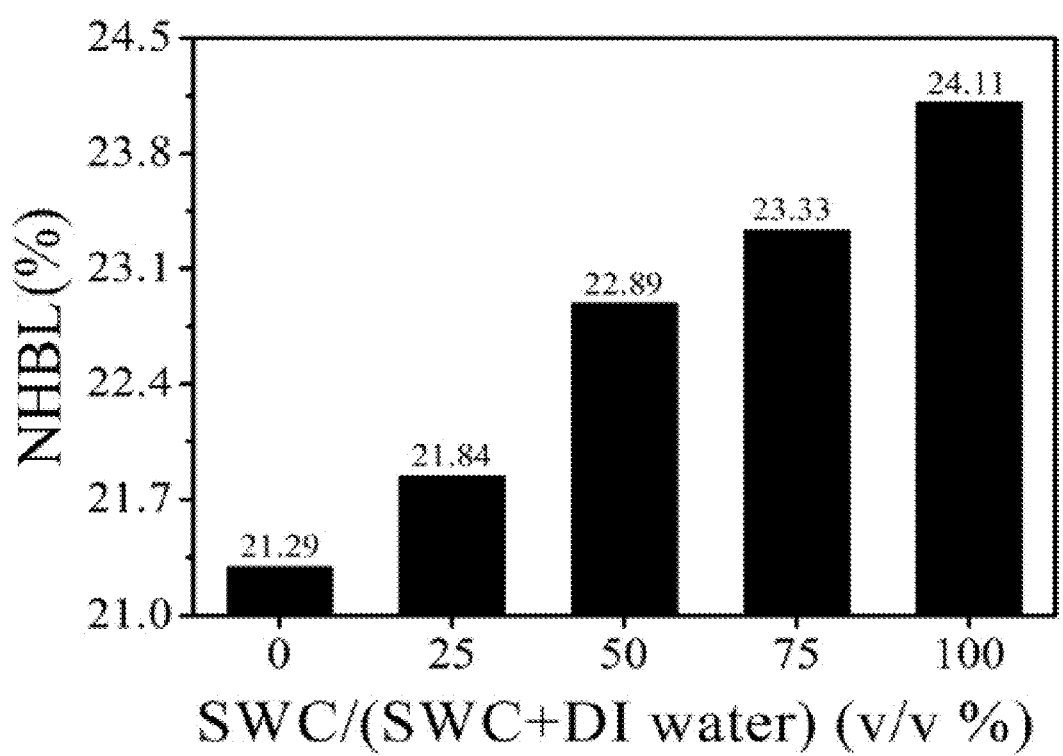
FIG. 5 shows the reduction of hydrogen bonds in water structures by small water cluster and deionized water.

Using the deionized water (0% small water cluster) as control (non-hydrogen bond level is 21.29%), the small water cluster of Example 1 is 24.11%. Compared to the deionized water, the non-hydrogen bond level of the small water cluster is 13% higher. When the ratios of the small water cluster are 25% (non-hydrogen bond level is 21.84%), 50% (non-hydrogen bond level is 22.89%) and 75% (non-hydrogen bond level is 23.33%), the non-hydrogen bond levels increase 2.6%, 7.5% and 9.6%, which shows a linear relationship between the concentration of the small water cluster (SWC) and the non-hydrogen bond level (NHBL) (see FIG. 5) with that in the small water cluster; the strong hydrogen bonds are broken to form weak hydrogen bonds and non-hydrogen bonds to form the structure of the small water cluster. Therefore, the small water cluster has specific properties and functions.

Example 4

Figure 6:
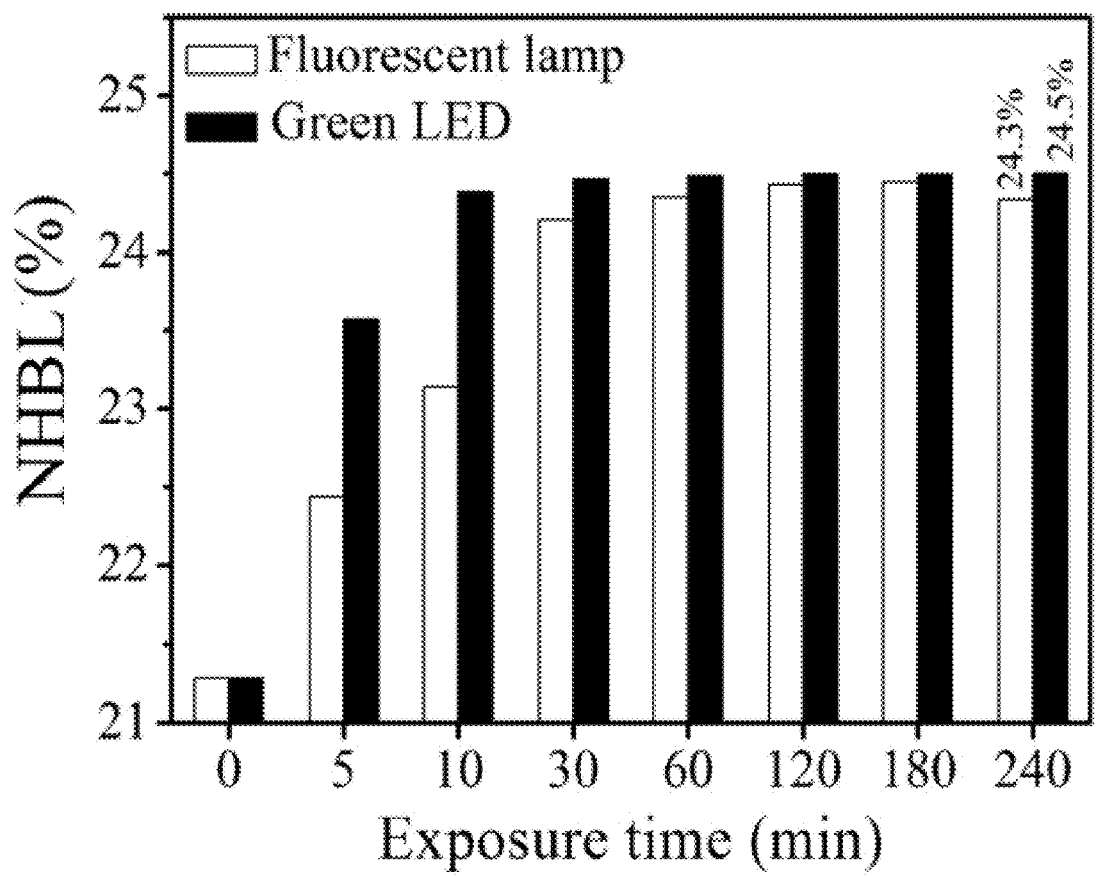
FIG. 6 shows the effect of different light exposure times on the production of small water cluster.

Effects of Different Illumination Time and Different Light Source in Preparation of Small Water Cluster of the Invention 20 mL of the deionized water (DI water) was added to a 50 mL glass bottles with 20 mL nano-gold/ceramic particles. The bottles were placed on shakers with regular shaking frequency and illuminated with different light sources. The water samples were taken at different time points and measured by Raman spectroscopy to obtain OH vibration signals for band deconvolution assay to determine non-hydrogen bond level (NHBL). After illumination with a daylight lamp and LED green lamp (wavelength of 530 nm) for 240 minutes, the non-hydrogen bond levels of the small water cluster illuminated by both daylight lamp and LED lamp can achieve a saturation value of about 24.4%. However, using the LED green lamp for illumination provides energy concentrated at 530 nm wavelength and can produce a stronger SPR effect, so after about 10 minutes, the saturation value can be achieved. However, when the daylight lamp is used for illumination, the saturation value is achieved after about 120 minutes (see FIG. 6).

Example 5

Infrared Absorption Spectrum (IR) of Small Water Cluster of the Invention

Figure 7:
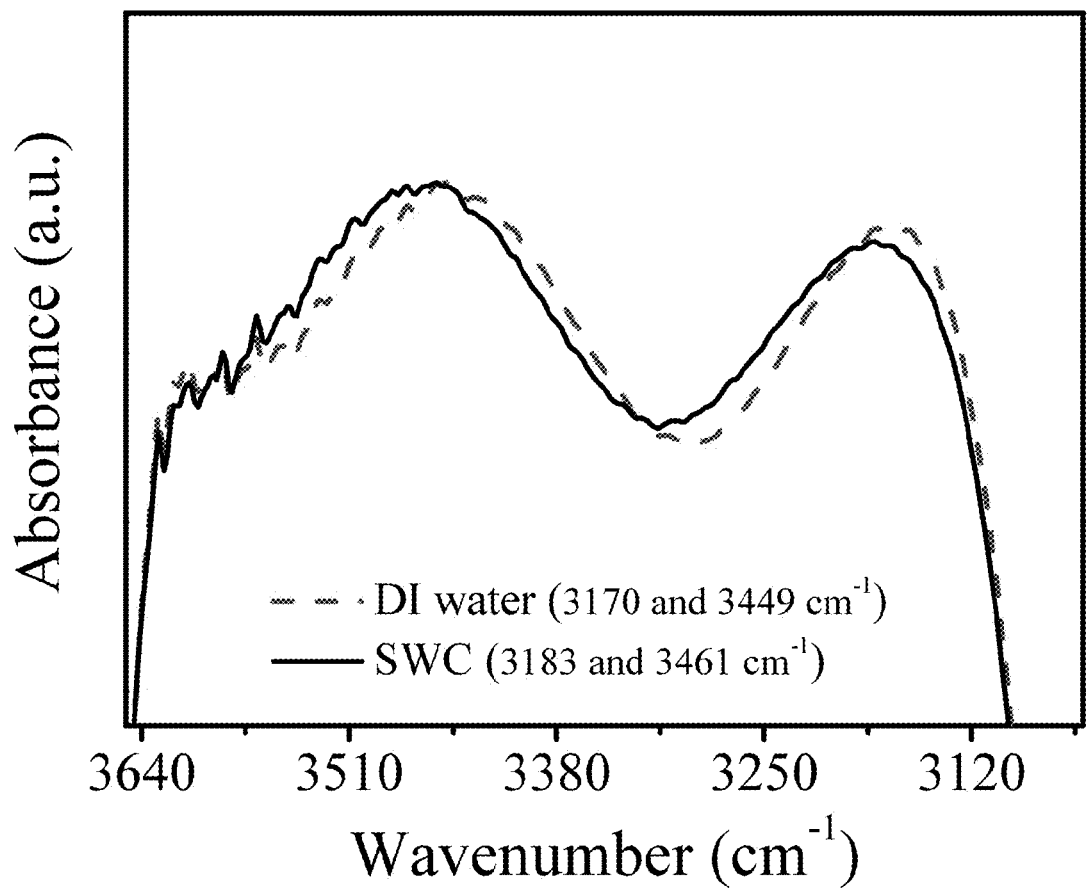
FIG. 7 shows the infrared absorption spectrum of the small water cluster and the deionized water; (a) deionized water (dashed line); (b) small water cluster (solid line).

Fourier-Transform Infrared Spectra of the deionized water (DI water; control) and the small water cluster (SWC) were measured by Fourier-Transform Infrared Spectrometer (Bruker-Tensor 27); the spectrum resolution was 8 $cm^{-1}$, and the scanning was repeated 30 times; the sample was injected into a Precision Demountable Cell of International Crystal and the thickness of polytetrafluoroethene separator was 0.015 mm. The OH vibration of water ranging from about 3090 to 3640 $cm^{-1}$ can be divided to two parts; the characteristic peak at wavelength of about 3090 to about 3310 $cm^{-1}$ represents triple hydrogen bond (high density hydrogen bond) and the characteristic peak at wavelength of about 3310 to about 3640 $cm^{-1}$ represents non-hydrogen bond, single hydrogen bond and doublet hydrogen bond (J. Phys. Chem. B, 2012, 116, 10609). After the deionized water was treated with nano-gold/ceramic particles, the characteristic peaks shifted to 3170 to 3183 $cm^{-1}$ and 3449-3461 $cm^{-1}$, respectively (see FIG. 7). This shows that the interaction between water molecules becomes weakened (Phys. Chem. Chem. Phys., 1999, 1, 4619), so nano-gold/ceramic particle treatment can break the hydrogen bonds between water molecules to form small water cluster.

Example 6

Vaporization Rate of Small Water Cluster of the Invention

Compared to the deionized water (DI water; control), the small water cluster (SWC) of Example 1 shows a 13% increase in non-hydrogen bond level. Therefore, at normal temperature and pressure, the small water cluster evaporates quicker than the deionized water. However, after a period of time, the weak hydrogen bond and non-hydrogen bond levels of the small water cluster become the same as those of the deionized water, at which point the vaporization rate of the both will be the same. When preparing the small water cluster, the deionized water was placed in a flask with 20 mL nano-gold/ceramic particles on a plate shaking at a regular frequency so that the small water cluster produced on the surface of the nano-gold/ceramic particles can evaporate and separate from the particle surface and then the small water cluster can be continuously produced on the particle surface.

Figure 8:
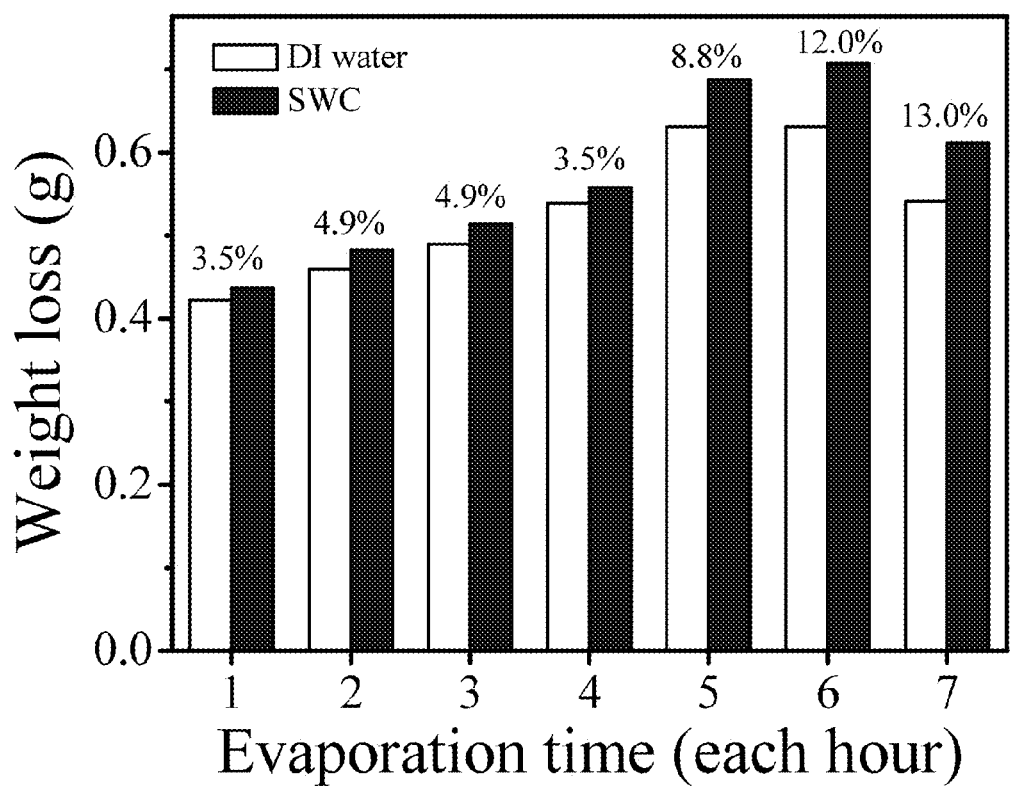
FIG. 8 shows the evaporation amount of the deionized water and the small water cluster per unit time (hour).

80 mL deionized water was added to a 250 mL flask and 80 mL water was added to a flask with 20 mL nano-gold/ceramic particles. The two flasks were placed on a plate shaking at a regular frequency and the reduced water amounts in the two flasks were measured hourly for 7 hours to determine the evaporated water amount. Each hour, the evaporated water amount of the deionized water and small water cluster may vary, whereas the evaporated water amount of the small water cluster is more than 3% higher than the deionized water. On average, the evaporated water amount of the small water cluster is 7.2% higher than the deionized water (see FIG. 8).

Example 7

Solubility of Small Water Cluster of the Invention 20 mL of each the small water cluster (SWC) of Example 1 and the deionized water (DI water) were added to sample bottles, respectively. Excess NaCl was added to the solutions, which were then mixed for 30 minutes. After standing for 30 minutes, the both bottles had unsolved solute. The 1 mL of saturated solution was weighed to determine the solubility of NaCl in 100 mL water of each solution. Moreover, solubility of tapimycin was also determined. 1.2 g of tapimycin was measured and added to each of two sample bottles. Then, the small water cluster and the deionized water were added to the bottles as solvent, respectively. After continuous mixing until no unsolved powder remained, the solute was totally solved to form a clear gel-like solution. The solubility of tapimycin per 100 mL water can be obtained based on the water (mL) needed to solve 1.2 g tapimycin.

The maximum amount of dissolved oxygen of the small water cluster of the invention was further measured. 40 mL of the small water cluster and the deionized water were added to 50 mL sample bottles, respectively. Gaseous oxygen was added to each water in bubble form for 30 minutes and the cap of each bottle was screwed tightly. After the water was left standing 5 minutes, the maximum amount of dissolved oxygen was measured by a portable dissolved oxygen meter (Lutron Electronic Enterprise Co., Ltd., Taiwan, Model: DO-5510).

The table below shows the solubility of different solutes in the small water cluster and the deionized water.

TABLE

The solubility of different solutes in the small water cluster and the deionized water (1 atm, 22.8° C.)

|  | NaCl (g dL$^{-1}$) | Tapimycin (g dL$^{-1}$) | Oxygen (mg L$^{-1}$) |
|---|---|---|---|
| Small water cluster | 41.3 | 140.6 | 23.8 |
| Deionized water | 36.2 | 104.5 | 20.3 |

It can be found from the above table that compared to the deionized water, the solubility of NaCl, tapimycin and oxygen in the small water cluster was 14%, 35% and 17% higher, respectively. This shows that the structure of the small water cluster is different from normal water and can effectively increase the solubility of solids and gas in water.

Example 8

Measurement of Amount of Small Water Cluster Dissolved in PEG400

The deionized water and the small water cluster were added to PEG400 solutions, respectively, to prepare a solution containing 10 wt % water. The water amounts in PEG400 solutions prepared by the deionized water and the small water cluster of the invention were measured by a moisture meter; the results were 10.97 wt % for deionized water and 10.44 wt % for the small water cluster of the invention. Since the small water cluster contains more free and available OH groups for vibration, it can form hydrogen bonds with PEG400 and the water molecules forming the hydrogen bond cannot react with Karl Fischer reagent, and thus the measured value is 4.8% less than the prepared value.

Example 9

Saturated Vapor Pressure of Small Water Cluster of the Invention

The measurement system was vacuumed before the experiment to remove other gas and then an appropriate amount of water was subjected to the system to start the experiment. The vapor pressure at 25° C. was measured at different time points until the vapor pressure remained constant. The constant vapor pressure is the saturated vapor pressure at this certain temperature. After 6 hours, the saturated vapor pressure of the deionized water and the small water cluster was 0.0316 bar and 0.0344 bar, respectively. Therefore, at the temperature of 25° C., the saturated vapor pressure of the small water cluster is higher than that of the deionized water by 8.9%.

TABLE

The saturated vapor pressure of the deionized water and the small water cluster at 25° C.

|  | 0 min (bar) | 30 min (bar) | 3 h (bar) | 6 h (bar) |
|---|---|---|---|---|
| Deionized water (24.8° C.) | 0.0208 | 0.0313 | 0.0313 | 0.0316 |
| Small water cluster (24.7° C.) | 0.0327 | 0.0356 | 0.0354 | 0.0344 |

Example 10

Assay of Removing DPPH Free Radicals by Small Water Cluster of the Invention

DPPH. (free radical of 2,2-diphenyl-1-pricrylhydrazyl) is a stable free radical customarily used in the measurement of electron paramagnetic resonance (EPR) (Journal of Food and Nutrition Research, Vol. 45, 2006, No. 1, pp. 1-11). DPPH in methanol or ethanol solution can be stably produced and detected by EPR. However, when it is reduced by antioxidants (AH) or free radicals (R.), the free radicals, DPPH., will be eliminate or reduced, so EPR measurement can be used to determine the ability of the small water cluster to remove free radicals.

Figure 9:
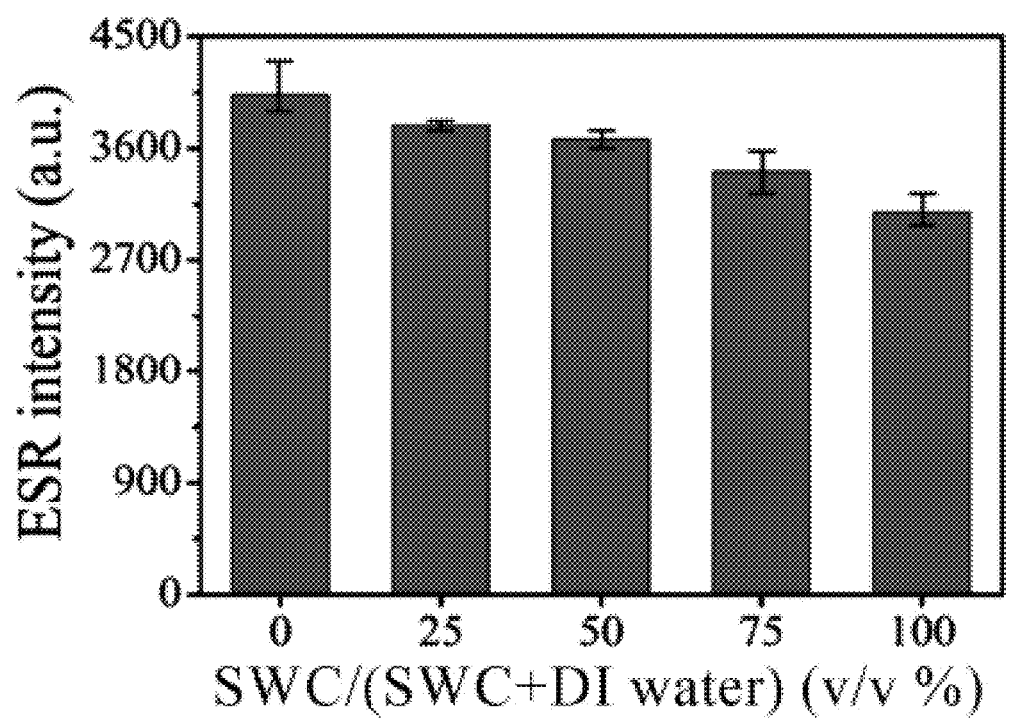
FIG. 9 shows the ability for removing DPPH free radicals by the small water cluster and the deionized water.

DPPH was added to methanol to obtain 4 nM DPPH in methanol solution. Different solutions with the ratios of the small water cluster to the deionized water were mixed with the 4 mM DPPH methanol solution in 1:1 volume ratio, respectively (the final concentration of DPPH is 2 mM), and then subjected to EPR measurement (Bruker EMX ESR spectrometer) after standing for two hours in the dark. The deionized water (0% small water cluster) was used as control and its EPR strength was 4033, while the ability of the small water cluster to remove DPPH free radicals was 24% higher. When the small water cluster is at a concentration of 25%, the EPR strength is 3783; at a concentration of 50%, the EPR strength is 3675; and at a concentration of 75%, the EPR strength is 3416 (see FIG. 9). The ability to remove DPPH free radicals is 6.2%, 8.9% and 15% for 25%, 50% and 75% small water cluster higher, respectively. It shows a linear relationship between the concentration of the small water cluster and removal of the free radical and that the small water cluster can effectively remove DPPH free radicals.

Example 11

Assay of Removing OH Free Radicals by Small Water Cluster of the Invention

Fenton's reagent can produce strong oxidative and non-selective OH free radical (.OH) in a reaction of H2O2 and Fe2+ ion and the .OH can oxidize the hard-degradable organic materials in wastewater. However, the OH free radical is a strong oxidant and thus may damage cell membranes, vessel walls, proteins and genes, cause aging and disease in the human body, and is harmful to human health. Since the OH free radicals produced by Fenton's reagent decay very rapidly, DMPO (5,5-dimethyl-1-pyrroline-N-oxide) should be added to capture the free radicals to produce DMPO-OH free radicals. Then, the free radical strength can be measured by EPR.

Fenton's reagent reaction was conducted to produce OH free radicals, to which 140 μL of deionized water (control group), the small water cluster and the filtrated water (positive control) were added, respectively. The filtrated water and small water cluster were produced in the same way as described in Example 2. Then, 20 μL phosphate buffer, 20 μL of 500 μM EDTA (Fe$^{2+}$/Ethylenediaminetetraacetic acid), 10 μL of 200 μM H$_2$O$_2$ and 10 μL of 2M DMPO were added to the solution. After reaction, DMPO-OH signal was measured by EPR.

Figure 10:
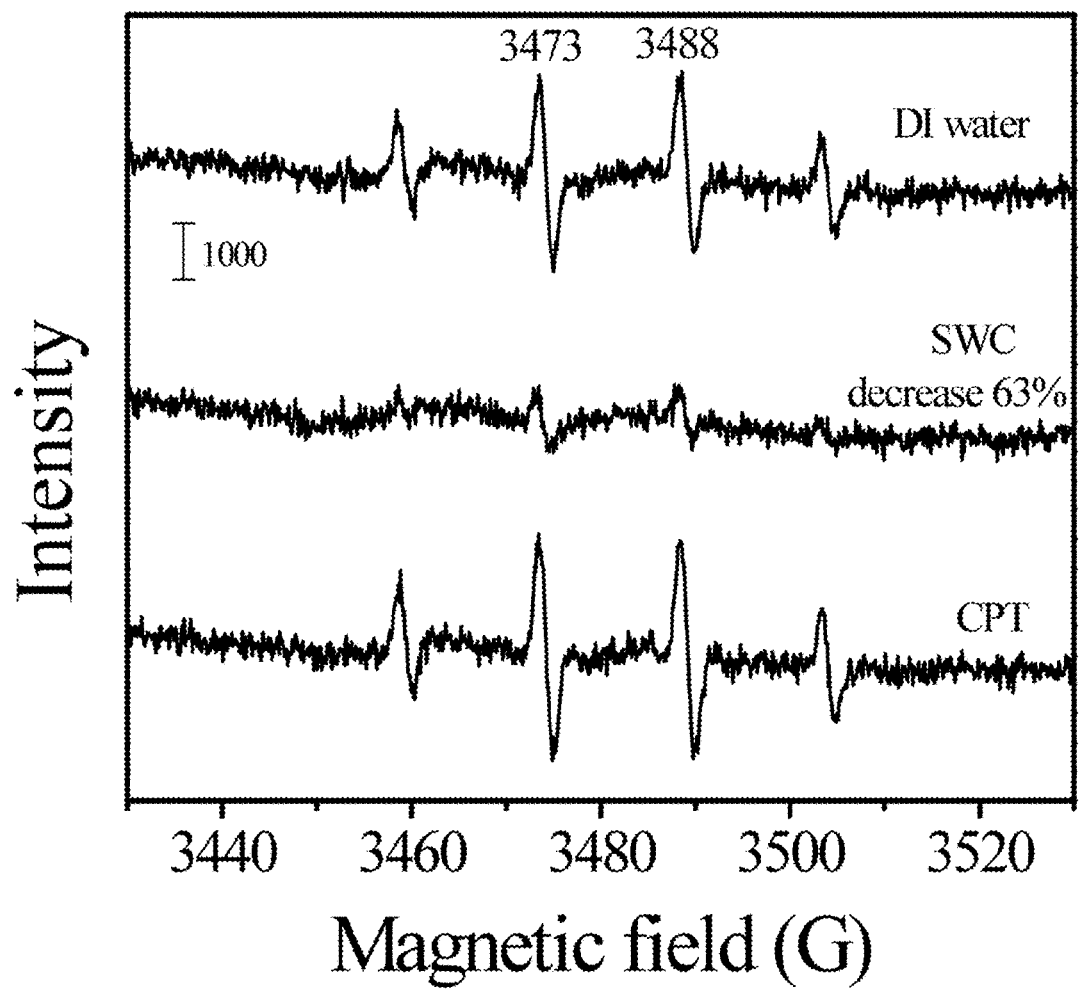
FIG. 10 shows the ability for removing hydroxyl free radicals in Fenton reagent by the small water cluster and the deionized water.

The Fenton's reagent prepared by the deionized water was used as the control group and that prepared by the small water cluster of the invention was used as experimental group. The results show that the small water cluster can effectively remove 63% of the free radicals. It was also found that the filtrated water cannot remove the free radicals. The above results show that the removal of free radicals is caused by the surface plasmon resonance effect after illuminating the nano-gold deposited on the surface of the ceramic particles (see FIG. 10).

Example 12

Assay of Reduction of NO Release by Small Water Cluster of the Invention

When the body's immune system is stimulated by a microorganism or its secreted substance (such as lipopolysaccharide (LPS) or lipoteichoic acid), reactive oxygen species (ROS) can be produced and production of NO induced. As a result, various inflammation reactions can be caused.

The measurement of the amount of NO was conducted by culturing RAW 264.7 cells, a rat macrophage cell line, purchased from American Type Culture Collection (ATCC) in a medium containing bovine fetal serum (10%), *penicillium* (100 unit/mL) and streptomycin (100 μg mL$^{-1}$) at 37° C. under 5% $CO_2$. After cultivation, the medium was added to the 96-well plate in a concentration ($2 \times 10^5$ cells/well) and then different concentrations of *E. coli* LPS (0-100 ng mL$^{-1}$) were added to the wells for cultivation for 24 hours. 100 μL of the medium was reacted with 100 μL of Griess reagent at room temperature for 10 minutes and the absorption value at 570 nm wavelength was measured by spectrophotometer (Labsystems, Helsinki, Finland) (Lin H C, Tsi S H, Chen C S, Chang Y C, Lee C M, Lai Z Y, Lin C M. Structure-activity relationship of coumarin derivatives on xanthine oxidase-inhibiting and free radical-scavenging activities. Biochemical Pharmacology. 2008, 75: 1416-1425).

Figure 11:
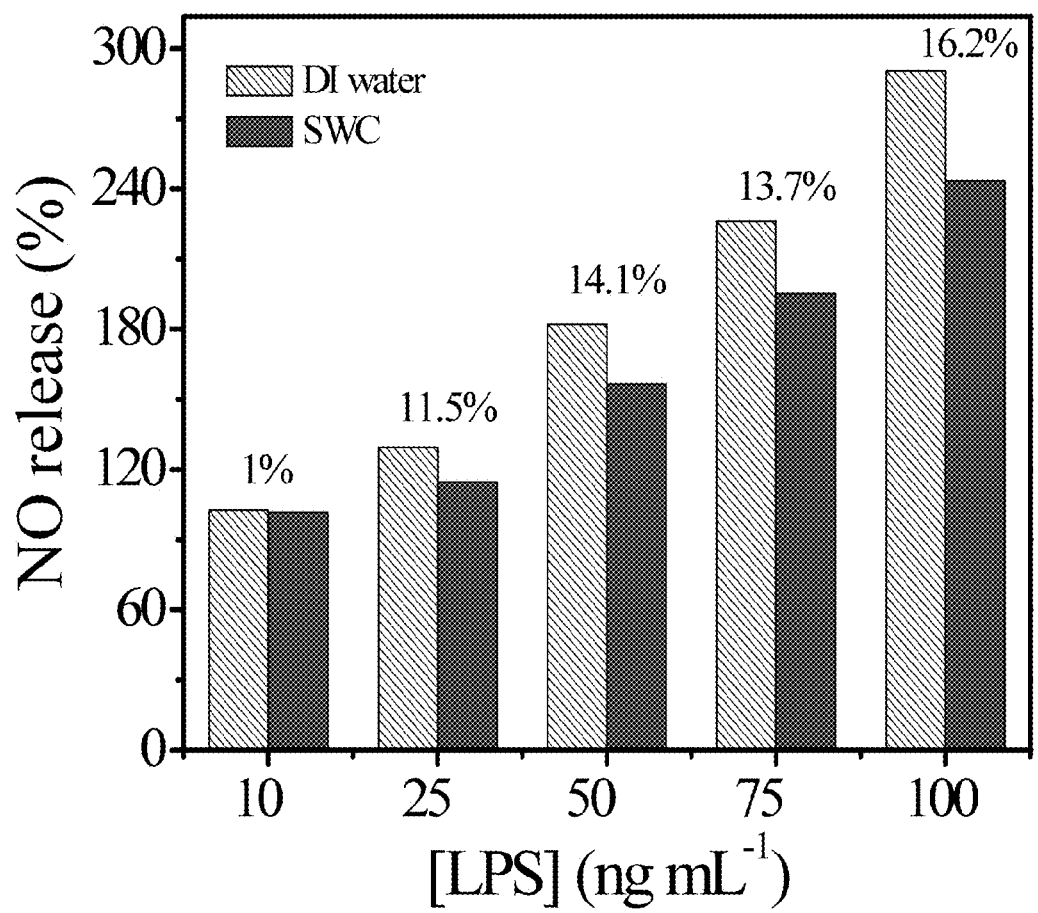
FIG. 11 shows the reduction of nitric oxide-releasing ability by the small water cluster in different LPS (an agent inducing cell inflammation) amounts.

The amount of LPS was increased from 10 ng mL$^{-1}$ to 25 ng ml$^{-1}$, 50 ng mL$^{-1}$, 75 ng mL$^{-1}$ and 100 ng mL$^{-1}$, and the small water cluster (SWC) of Example 1 was used as the solvent of the medium. Compared to the deionized water (DI water) as the solvent of the medium, the NO release amounts in the above concentrations of the small water cluster were 1.0%, 11.5%, 14.1%, 13.7% and 16.2% lower, respectively, so it shows that the small water cluster can effectively reduce the inflammation induced by LPS (see FIG. 11).

Example 13

Stability Assay of Small Water Cluster of the Invention

At 0, 1, 2, 3 and 5 days after preparation of the small water cluster of Example 1, the non-hydrogen bond levels were 24.11%, 23.52%, 23.11%, 22.11% and 21.39%, respectively. Compared to the non-hydrogen bond level of the deionized water, the small water cluster can stably exist for at least 3 days.

Example 14

Diffusion Assay of Small Water Cluster of the Invention

Figure 12:
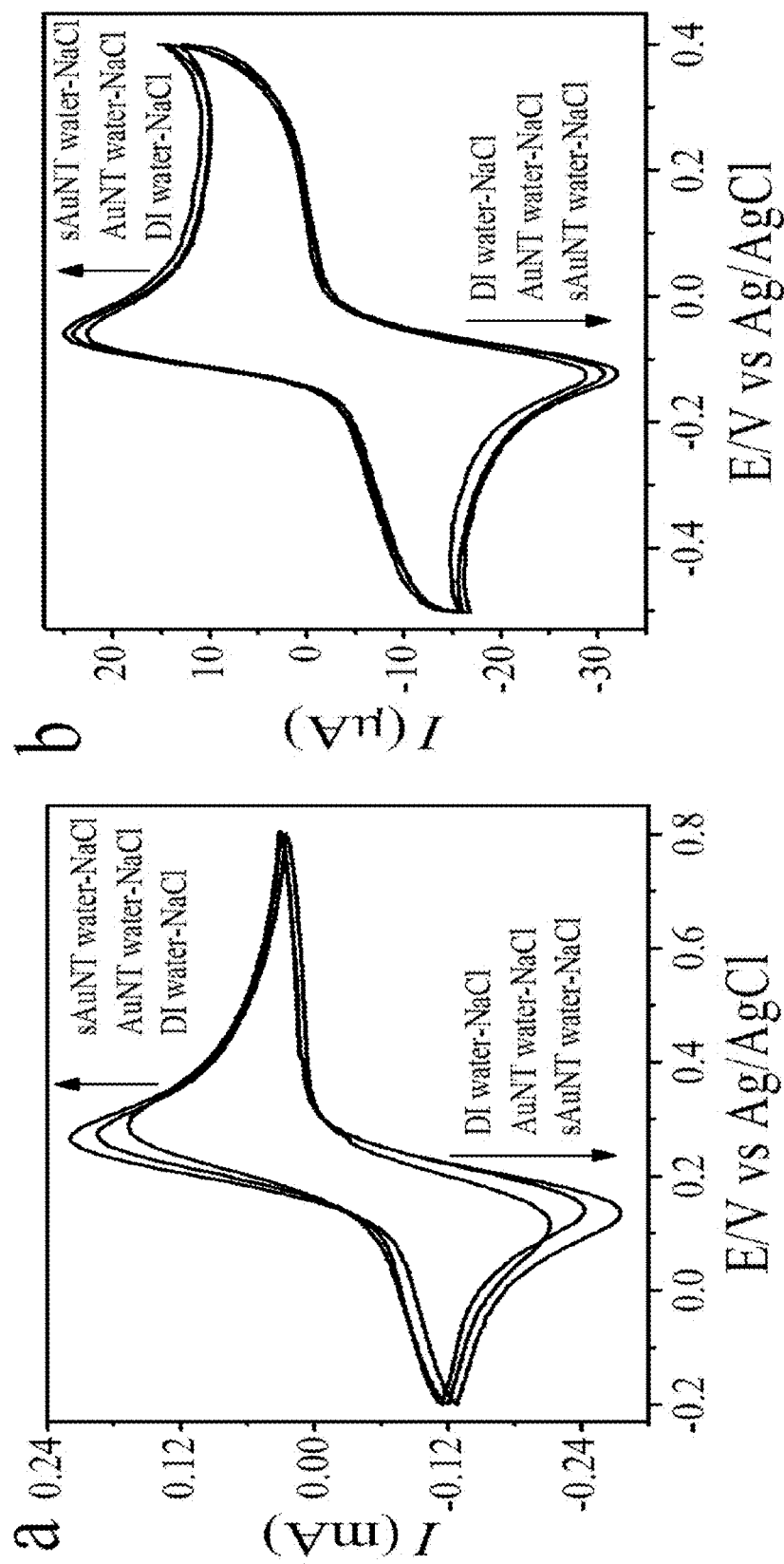
FIG. 12 shows the voltammetric data at a scan rate of 0.1 V s21 recorded in different water-based saline solutions at a 3 mm diameter planar Pt electrode for different systems; (a) 30 mM $K_3Fe(CN)_6$ for one electron participating in the reaction; (b) 1 mM HQ for two electrons participating in the reaction.

The water treated with nano-gold in combination with illumination has a weak hydrogen bond, which is responsible for its novel diffusion properties. FIG. 12 shows cyclic voltammograms in different water-based saline solutions (DI water-NaCl for the saline prepared by deionized water; AuNT water-NaCl for the saline prepared by the small water cluster treated by the nano-gold in combination with illumination by daylight lamp; and sAuNT water-NaCl for the saline prepared by the molecular cluster water treated by the nano-gold in combination with illumination by green LED lamp) for $K_3Fe(CN)_6$ (FIG. 12(*a*)) and hydroquinone (HQ) (FIG. 12 (*b*)), from which the diffusion coefficients of $K_3Fe(CN)_6$ and HQ in saline solution can be obtained. Encouragingly, the calculated diffusion coefficient of $K_3Fe(CN)_6$ increased from $2.76 \times 10^{-6}$ cm s$^{-1}$ ($1.78 \times 10^{-6}$ cm s$^{-1}$ for HQ) to $3.59 \times 10^{-6}$ cm s$^{-1}$ ($2.0 \times 10^{-6}$ cm s$^{-1}$ for HQ) when using AuNT water instead of conventional DI water. This is an increase of 30% (12% for HQ) for the diffusion coefficient. This increased to 67% (24% for HQ) using AuNT water prepared using green LED illumination ($4.62 \times 10^{-6}$ cm s$^{-1}$ for $K_3Fe(CN)_6$; $2.20 \times 10^{-6}$ cm s$^{-1}$ for HQ). From the above results, the diffusion effect of the untreated saline prepared by deionized water is the worst, and that of the saline prepared by the small water cluster treated by the nano-gold in combination with illumination by green LED lamp (sAuNT water-NaCl) is better than the saline prepared by the small water cluster treated by the nano-gold in combination with illumination by daylight lamp (AuNT water-NaCl).

Example 15

Blood Dialysis Assay of Small Water Cluster of the Invention

Figure 13:
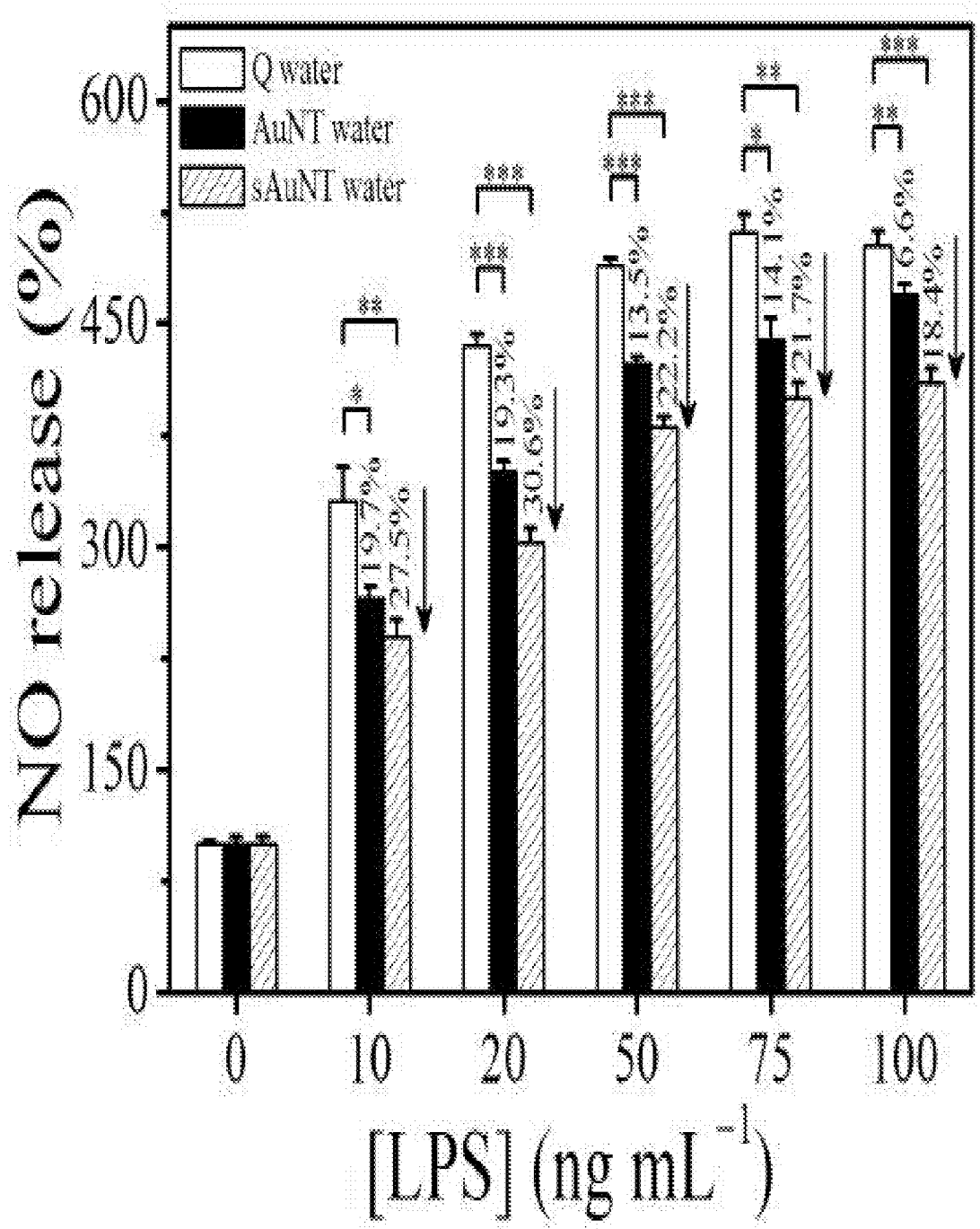
FIG. 13 shows the anti-oxidative activity of AuNT water (■) and sAuNT water (▨) compared to DI water (▢) on reduction of lipopolysaccharide (LPS)-induced NO release with dose of LPS. Determination of nitric oxide (NO) production was made following the method shown in the literature (see SD). DI water, AuNT water and sAuNT water were used for medium preparation. *p=0.05; p=0.01; *p=0.001.
Figure 14:
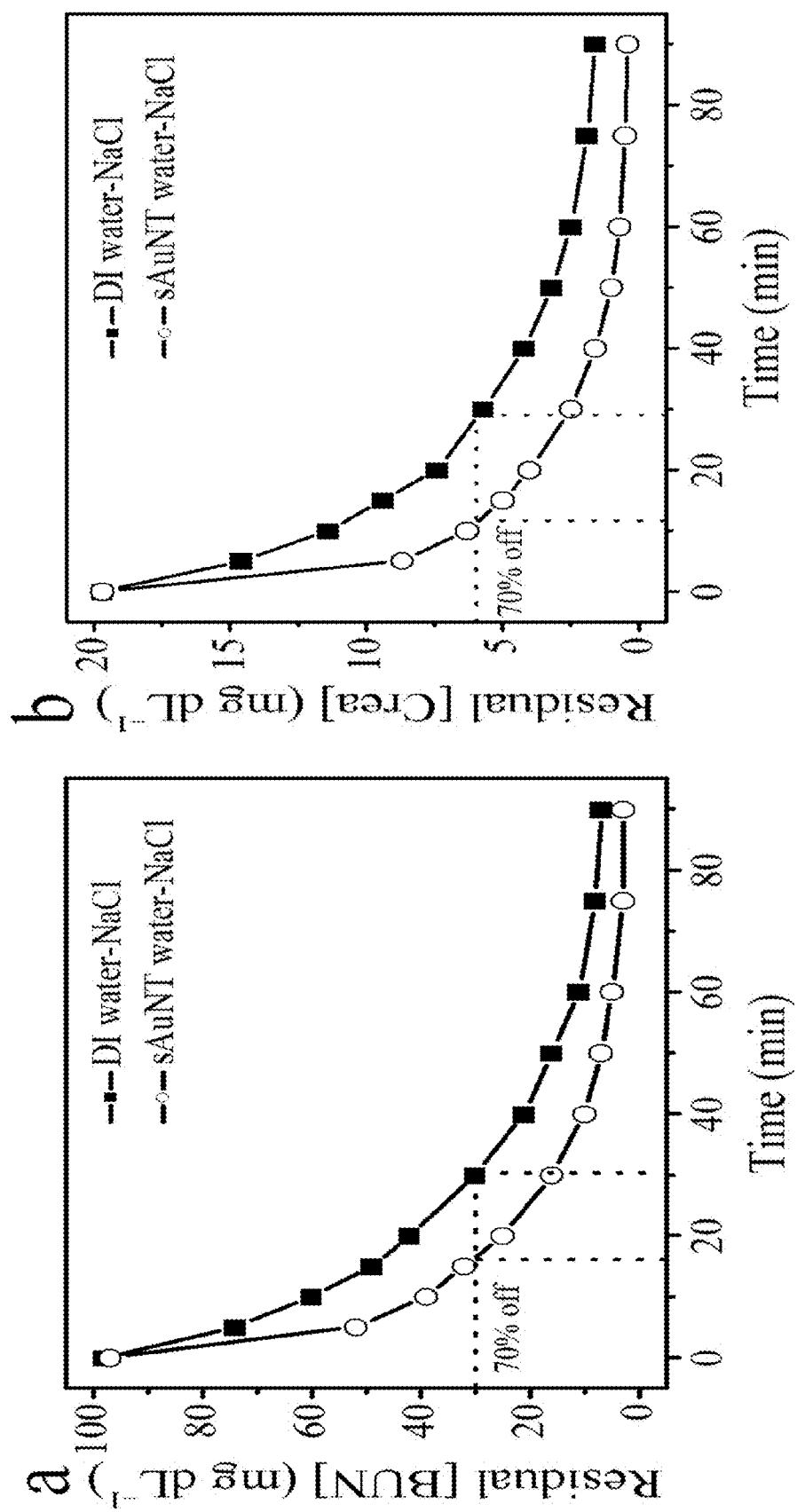
FIGS. 14 (a) and (b) show the removal efficiencies of BUN and Crea by using saline solutions based on different water; (a) removal efficiencies of BUN by using different saline solutions; treatment times for removal of 70% BUN (initially ca. 100 mg dL21) are ca. 30 and 16 min by using saline solution (DI) and using saline solution (sAuNT), respectively; (b) removal efficiencies of Crea by using different saline solutions. Treatment times for removal of 70% Crea (initially ca. 20 mg dL21) are ca. 29 and 12 min by using saline solution (DI) and using saline solution (sAuNT), respectively.

As shown in Example 1, water was treated by nano-gold surface plasmon resonance to obtain the small water cluster and then the small water cluster was used to prepare the hemodialysis solution. The reduction of NO release induced by LPS mentioned in Example 12 was used to evaluate the anti-inflammation effect of the small water cluster. FIG. 13 shows the anti-inflammation effect of the hemodialysis solutions prepared by AuNT water-NaCl and sAuNT water-NaCl, which is evaluated by the reduction of NO release induced by LPS, compared to the hemodialysis solution prepared by DI water-NaCl. As shown in FIGS. 14 (*a*) and (*b*), the treatment times for the removal of 70% BUN (100 mg dL21) in blood are ca. 30 and 16 min using saline solution (DI) and saline solution (sAuNT), respectively (see FIG. 14 (*a*)). The treatment times for the removal of 70% Crea (20 mg dL21) in blood are ca. 29 and 12 min using saline solution (DI) and saline solution (sAuNT), respectively. These results suggest that the treatment times for the removal of 70% BUN and Crea can be reduced by 47% and 59%, respectively, using AuNT water instead of DI water in dialysate of saline solution (see FIG. 14 (*b*)). As shown in the above results, the hemodialysis effect of the untreated saline prepared by deionized water is the worst, and that of the saline prepared by the small water cluster treated by the nano-gold in combination with illumination by green LED lamp (sAuNT water-NaCl) is better than the saline prepared by the small water cluster treated by the nano-gold in combination with illumination by daylight lamp (AuNT water-NaCl).

Figure 15:
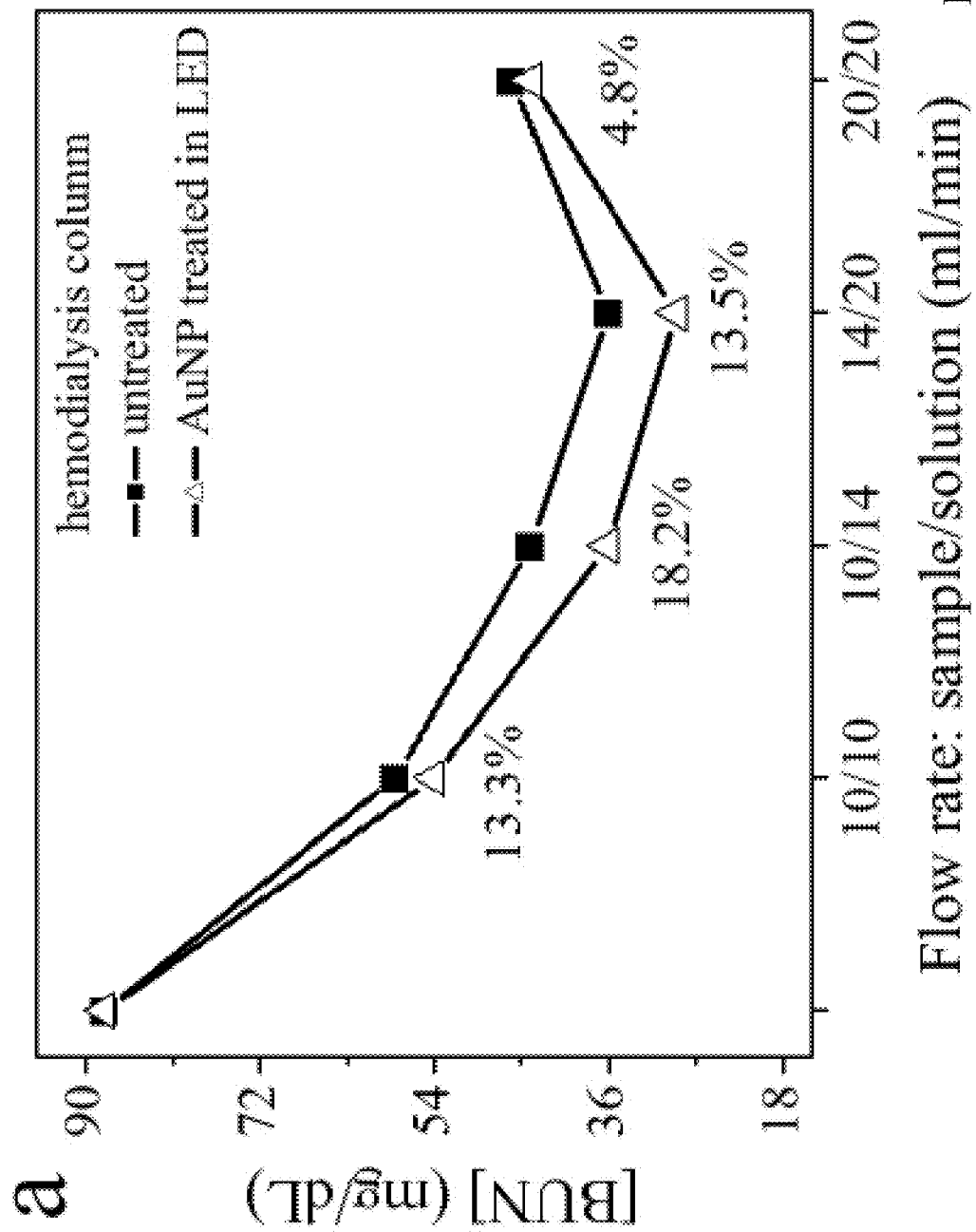
FIGS. 15 (a), (b) and (c) show in vitro haemodialysis simulation assay. During dialysis, AK column (B3-1.0 A) was coated with nano-gold and subjected to illumination to remove BUN (a), Crea (b) and other medium molecules in blood (B12) (c).
Figure 15:
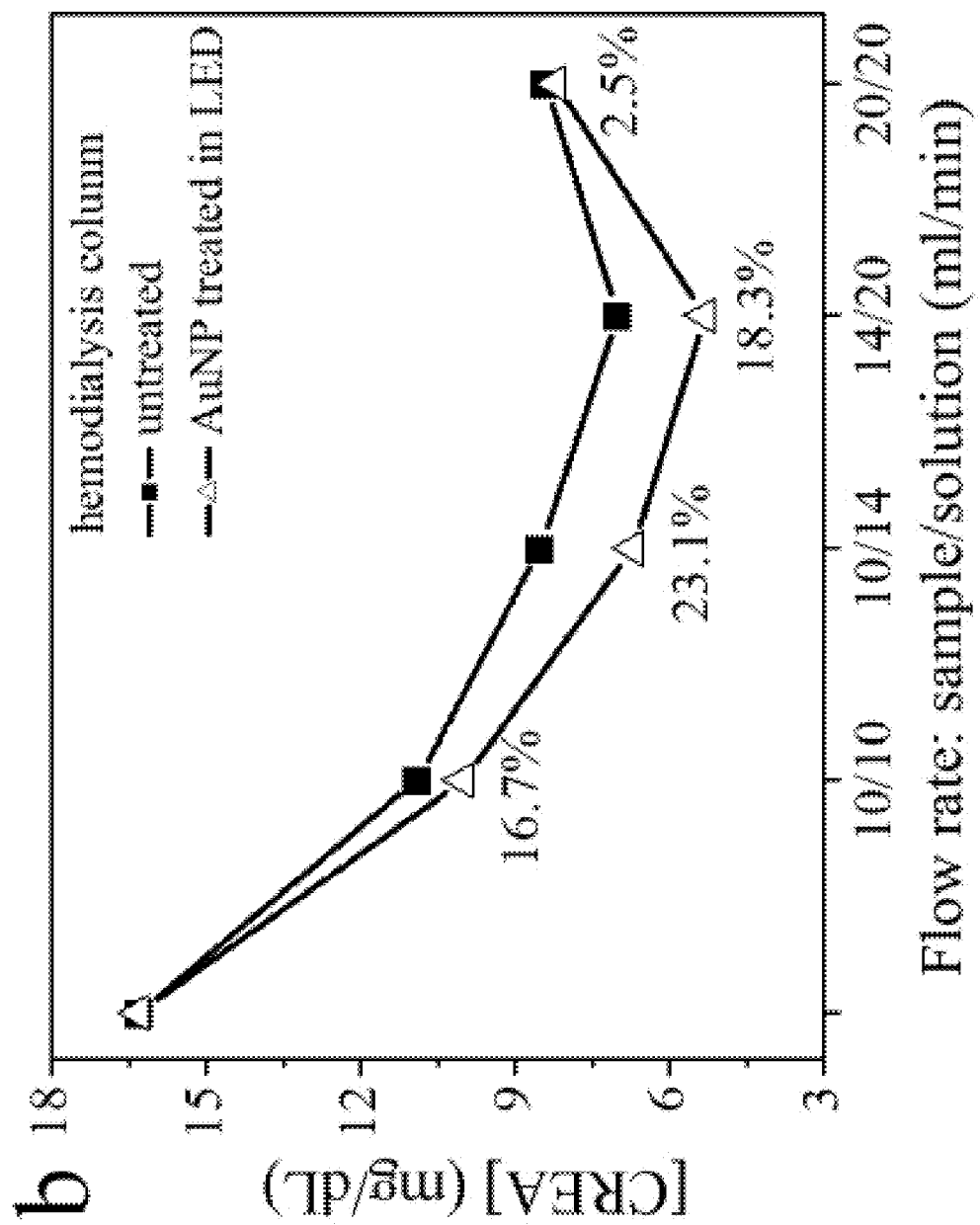
Figure 15:
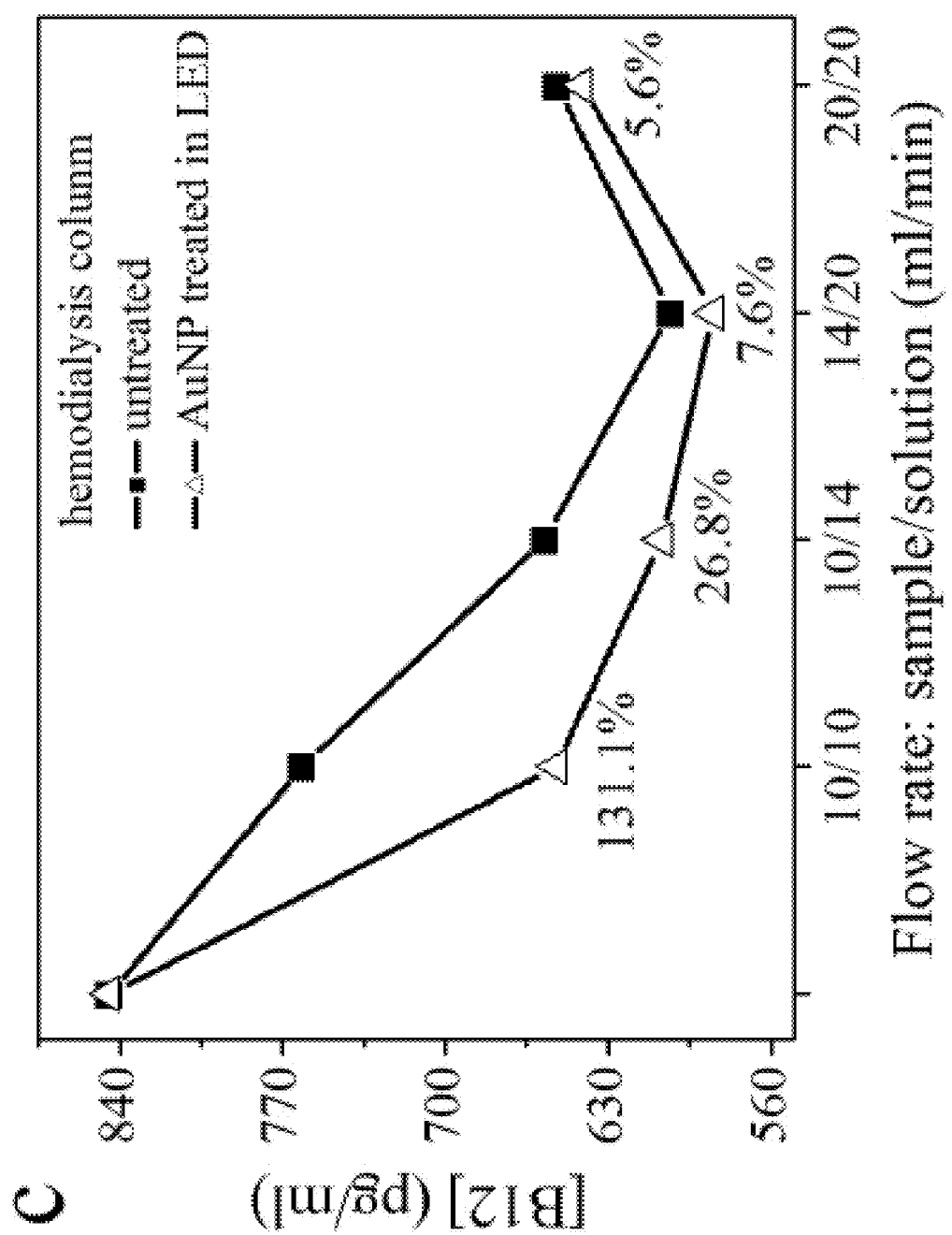

Alternatively, to conduct an in vitro hemodialysis assay, the AK column (B3-1.0 A) used in hemodialysis was coated with nano-gold and illuminated during the hemodialysis and the small water cluster were simultaneously produced. The samples containing BUN, Crea and other medium molecules (B12) were passed through the AK columns with different flow rates wherein "untreated" represents the AK column without the nano-gold coating and illumination and the "AuNP treated in LED" represents the AK column coated with the nano-gold and treated with illumination by green LED lamp. The hemodialysis solutions were prepared by DI water. The results are shown in FIGS. 15 (a), (b) and (c). FIG. 15 (a) shows the efficiency of removing BUN, FIG. 15 (b) shows the efficiency of removing Crea and FIG. 15 (c) shows the efficiency of removing B12. As shown in FIG. 15, the removal rates of BUN, Crea and B12 by the AK column coated with nano-gold in combination with illumination are better than that of the untreated AK column.

Example 16

PCR Reaction Using Small Water Cluster of the Invention

Figure 16:
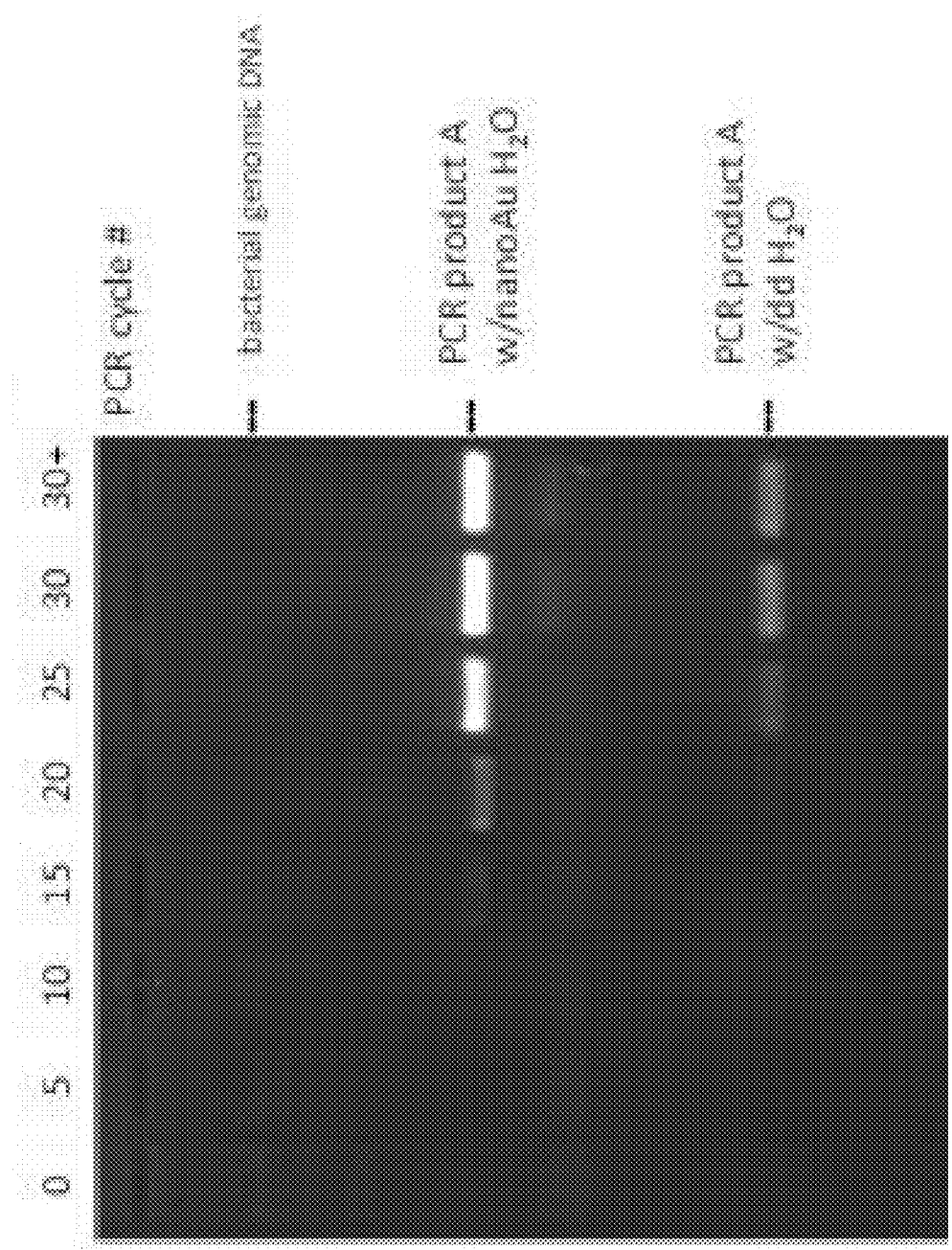
FIG. 16 shows the gel electrophoresis of PCR reaction using the small water cluster of the invention.

The small water cluster of Example 1 was used to conduct a PCR reaction using 1 mg DNA template, 0.5 nM primer, 0.2 mM dNTP and 0.5 U/ml Taq polymerase. Then, the PCR product was subjected to electrophoresis with TAE argose gel. The qnrB bacterial gene fragment was used to conduct a PCR reaction in the small water cluster; the PCR rate of the product A (amplified qnrB bacterial gene fragment) increased 20-fold compared to the deionized water. The result shows that the small water cluster can effectively increase the PCR reaction rate (see FIG. 16).

What is claimed is:

1. A small water cluster, which has one of the following characteristics:
    (a) the central points of the Raman bands in the deconvoluted spectrum on OH vibration of water are at the positions of about 3018 $cm^{-1}$, about 3223 $cm^{-1}$, about 3393 $cm^{-1}$, about 3506 $cm^{-1}$, and 3624 $cm^{-1}$ respectively, and the non-hydrogen bond level obtained by the integral area at the about 3506 $cm^{-1}$ and about 3624 $cm^{-1}$ positions divided by the sum of the integral areas of the five bands at about 3018 $cm^{-1}$, about 3223 $cm^{-1}$, about 3393 $cm^{-1}$, about 3506 $cm^{-1}$, and 3624 $cm^{-1}$ positions is higher than about 22%;
    (b) the characteristic peak of the triple hydrogen bond in the IR spectrum (about 3090 to about 3310 $cm^{-1}$) and the non-hydrogen bond, single hydrogen bond and doublet hydrogen bond in the IR spectrum (about 3310 $cm^{-1}$ to about 3640 $cm^{-1}$) of the water molecule shift from about 3170 $cm^{-1}$ to more higher than about 3175 $cm^{-1}$ and from about 3449 $cm^{-1}$ to more higher than about 3454 $cm^{-1}$, respectively;
    (c) the evaporation rate of the small water cluster of the invention is more than 3%/hour higher than that of deionized water;
    (d) the solubility of NaCl in the small water cluster at about 22.8° C. under about 1 atmosphere is more than about 37 g $dL^{-1}$;
    (e) the maximum amount of dissolved oxygen of the small water cluster at about 22.8° C. under about 1 atmosphere is more than about 21 mg $L^{-1}$;
    (f) the solubility of the small water cluster in PEG 400 is smaller than the preparation value by more than about 2%; and
    (g) the saturated vapor pressure of the small water cluster at 25° C. is higher than that of the deionized water by more than about 3.0%.

2. The small water cluster of claim 1, wherein the small water cluster has metal residue more than about 0.05 ppb measured by inductively coupled plasma-mass spectrometer (ICP-MS).

3. The small water cluster of claim 1, wherein (a) the Raman spectrum further comprises the Raman shifts at the about 3506 $cm^{-1}$ and 3624 $cm^{-1}$ positions higher than 15.0% and 6%, respectively, wherein the percentage is calculated by the integral area of the band at about 3506 $cm^{-1}$ or at about 3624 $cm^{-1}$ divided by the sum of the integral areas of the five bands at about 3018 $cm^{-1}$, about 3223 $cm^{-1}$, about 3393 $cm^{-1}$, about 3506 $cm^{-1}$, and 3624 $cm^{-1}$ positions; (b) the characteristic peak of the triple hydrogen bond in the IR spectrum (about 3090 to about 3310 $cm^{-1}$) and the non-hydrogen bond, single hydrogen bond and doublet hydrogen bond in the IR spectrum (about 3310 $cm^{-1}$ to about 3640 $cm^{-1}$) of the water molecule shift from about 3170 $cm^{-1}$ to about 3180 $cm^{-1}$ and from about 3449 $cm^{-1}$ to about 3461 $cm^{-1}$, respectively; (c) the evaporation rate of the small water cluster is more than 7.2%/hour higher than that of the deionized water; (d) the solubility of NaCl in the small water cluster of the invention at about 22.8° C. under about 1 atmosphere is more than about 41.3 g $dL^{-1}$; or (e) the maximum amount of dissolved oxygen of the small water cluster at about 22.8° C. under about 1 atmosphere is more than about 23.8 mg $L^{-1}$.

4. The small water cluster of claim 1, which can stably exist for at least three days.

* * * * *